ID

US012137687B2

(12) United States Patent
Zeier et al.

(10) Patent No.: US 12,137,687 B2
(45) Date of Patent: Nov. 12, 2024

(54) METHOD FOR INDUCING ACQUIRED RESISTANCE IN A PLANT

(71) Applicant: HEINRICH HEINE UNIVERSITAET DUESSELDORF, Duesseldorf (DE)

(72) Inventors: Juergen Zeier, Duesseldorf (DE); Michael Bernd Hartmann, Duesseldorf (DE)

(73) Assignee: HEINRICH HEINE UNIVERSITAET DUESSELDORF, Duesseldorf (DE)

( * ) Notice: Subject to any disclaimer, the term of this patent is extended or adjusted under 35 U.S.C. 154(b) by 471 days.

(21) Appl. No.: 16/763,737

(22) PCT Filed: Nov. 15, 2018

(86) PCT No.: PCT/EP2018/081355
§ 371 (c)(1),
(2) Date: May 13, 2020

(87) PCT Pub. No.: WO2019/096896
PCT Pub. Date: May 23, 2019

(65) Prior Publication Data
US 2020/0367495 A1 Nov. 26, 2020

(30) Foreign Application Priority Data

Nov. 15, 2017 (EP) .................................... 17201923

(51) Int. Cl.
*A01N 43/40* (2006.01)
*A01H 3/04* (2006.01)
*C05G 1/00* (2006.01)

(52) U.S. Cl.
CPC ............... *A01N 43/40* (2013.01); *A01H 3/04* (2013.01); *C05G 1/00* (2013.01)

(58) Field of Classification Search
CPC ............. A01N 43/40; A01H 3/04; C05G 1/00
See application file for complete search history.

(56) References Cited

U.S. PATENT DOCUMENTS

| | | | |
|---|---|---|---|
| 4,054,668 A | 10/1977 | Kirino et al. | |
| 4,684,483 A | 8/1987 | Richard et al. | |
| 2016/0037772 A1* | 2/2016 | Guerrero Mendez | A01N 37/42 504/142 |
| 2019/0159449 A1* | 5/2019 | Jiménez Arias | A01N 43/40 |

FOREIGN PATENT DOCUMENTS

WO    WO-2017158225 A1 * 9/2017 ............. A01N 33/06

OTHER PUBLICATIONS

Chen, et al., N-hydroxy-pipecolic acid is a Mobile Metabolite That Induces Systemic Disease Resistance in *Arabidopsis*, May 2018, PNAS, vol. 115, No. 21, pp. E4920-E4929. (Year: 2018).*
Raj, S. Niranjan, et al. "Applications of biopolymers in agriculture with special reference to role of plant derived biopolymers in crop protection." Biopolymers: Biomedical and Environmental Applications, eds S. Kalia, and L. Avérous (Hoboken, NJ: Wiley Publishing LLC) (2011): 461-481. (Year: 2011).*
Brecher et al. Pure Appl. Chem., vol. 80, No. 2, pp. 277-410, 2008. (Year: 2008).*
Bartsch, M., Gobbato, E., Bednarek, P., Debey, S., Schultze, J.L., Bautor, J., and Parker, J.E. (2006). Salicylic acid-independent Enhanced Disease Susceptibility1 signaling in *Arabidopsis* immunity and cell death is regulated by the monoxygenase FMO1 and the nudix hydrolase NUDT7. Plant Cell 18: 1038-1051.
Bernsdorff, F., Döring, A.-C., Gruner, K., Schuck, S., Bräutigam, A., and Zeier, J. (2016). Pipecolic acid orchestrates plant systemic acquired resistance and defense priming via salicylic acid-dependent and -independent pathways. Plant Cell 28: 102-129.
Ding, P., Rekhter, D., Ding, Y., Feussner, K., Busta, L., Haroth, S., Xu, S., Li, X., Jetter, R., Feussner, I., and Zhang, Y. (2016). Characterization of a pipecolic acid biosynthesis pathway required for systemic acquired resistance. Plant Cell 28, 2603-2615.
Hartmann, M., Kim, D., Bernsdorff, F., Ajami-Rashidi, Z., Scholten, N., Schreiber, S., Zeier, T., Schuck, S., Reichel-Deland, V., and Zeier, J. (2017). Biochemical principles and functional aspects of pipecolic acid biosynthesis in plant immunity. Plant Physiol. 174, 124-153.
Hartmann, M., Zeier, T., Bernsdorff, F., Reichel-Deland, V., Kim, D., Hohmann, M., Scholten, N., Schuck, S., Bräutigam, A., Hölzel, T., Ganter, C., and Zeier, J. (2018). Flavin monooxygenase-generated N-hydroxypipecolic acid is a critical element of plant systemic immunity. Cell 173, 456-469.
Huijbers, M.M., Montersino, S., Westphal, A.H., Tischler, D., and van Berkel, W.J. (2014). Flavin dependent monooxygenases. Arch. Biochem. Biophys. 544, 2-17.

(Continued)

*Primary Examiner* — Mina Haghighatian
*Assistant Examiner* — Janice Y Silverman
(74) *Attorney, Agent, or Firm* — RAPHAEL BELLUM PLLC

(57) ABSTRACT

The present invention generally relates to the field of plant protection products and concerns a method for inducing acquired resistance in a plant to a plant pathogen, comprising obtaining or providing a composition comprising 1-hydroxypiperidine-2-carboxylic acid or a salt or derivative thereof, and contacting a plant with said composition, thereby inducing acquired resistance in the plant to the plant pathogen. Further, the present invention relates to the use of 1-hydroxypiperidine-2-carboxylic acid or a salt or derivative thereof for inducing acquired resistance in a plant to a plant pathogen. Also encompassed by the present invention are a plant seed coated with a composition comprising 1-hydroxypiperidine-2-carboxylic acid or a salt or derivative thereof, an irrigation system filled with irrigation water comprising 1-hydroxypiperidine-2-carboxylic acid or a salt or derivative thereof in a concentration of at least 0.1 mM, and a composition comprising 1-hydroxypiperidine-2-carboxylic acid or a salt or derivative thereof in a concentration of at least 0.1 mM, and a plant nutrient and/or a further plant protection product or a salt or derivative thereof.

14 Claims, 11 Drawing Sheets

(56) References Cited

OTHER PUBLICATIONS

Figure 1:
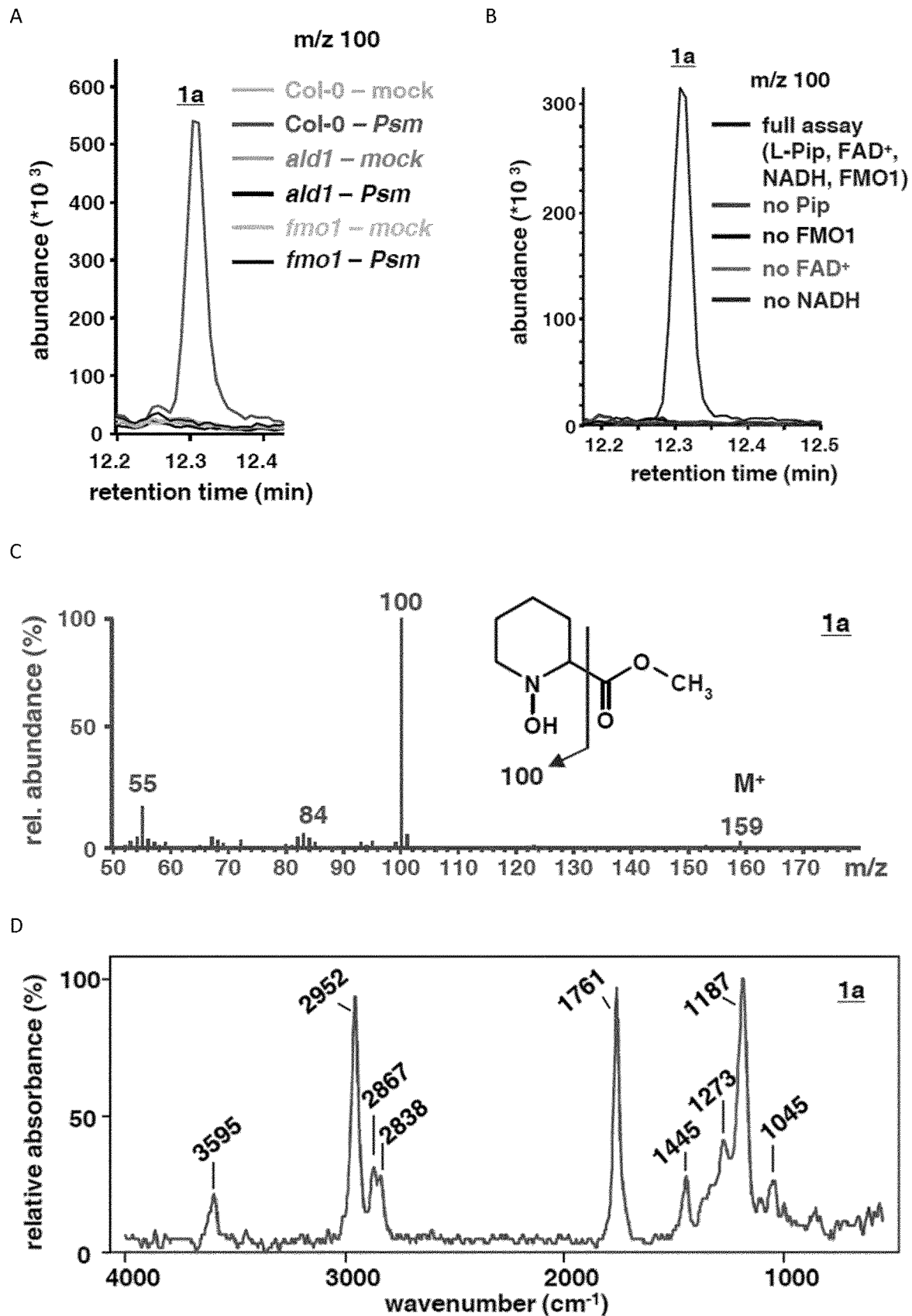

Jung, G.Y., Park, J.Y., Choi, H.J., Yoo, S.-J., Park, J.-K., and Jung, H.W. (2016). A Rice Gene Homologous to *Arabidopsis* AGD2-Like Defense1 Participates in Disease Resistance Response against Infection with Magnaporthe bryzae. Plant Pathol. J. 32, 357-362.

Koch, M., Vorwerk, S., Masur, C., Sharifi-Sirchi, G., Olivieri, N., and Schlaich, N.L. (2006). A role for a flavin-containing monooxygenase in resistance against microbial pathogens in *Arabidopsis*. Plant J 47: 629-639.

Mishina, T.E., and Zeier, J. (2006). The *Arabidopsis* flavin-dependent monooxygenase FMO1 is an essential component of biologically induced systemic acquired resistance. Plant Physiol 141: 1666-1675.

Murahashi, S.-I., and Shiota, T. (1987). Short-step synthesis of amino acids and N-hydroxyamino acids from amines. Tetrahedron Lett. 28, 6469-6472.

Návarová, H., Bernsdorff, F., Dóring, A.-C., and Zeier, J. (2012). Pipecolic acid, an endogenous mediator of defense amplification and priming, is a critical regulator of inducible plant immunity. Plant Cell 24: 5123-5141.

Olszak, B., Malinovsky, F.G., Brodersen, P., Grell, M., Giese, H., Petersen, M., and Mundy, J. (2006). A putative flavin-containing mono-oxygenase as a marker for certain defense and cell death pathways. Plant Sci. 170, 614-623.

Pálfi, G., and Dézsi, L. (1968). Pipecolic acid as an indicator of abnormal protein metabolism in diseased plants. Plant Soil 29: 285-291.

Schlaich, N. L. (2007). Flavin-containing monooxygenases in plants: looking beyond detox. Trends Plant Sci. 12: 412-418.

Sharma, S., Shinde, S., and Verslues, P.E. (2013). Functional characterization of an ornithine cyclodeaminase-like protein of *Arabidopsis thaliana*. BMC Plant Biol. 13, 182.

Song, J.T., Lu, H., McDowell, J.M., and Greenberg, J.T. (2004a). A key role for ALD1 in activation of local and systemic defenses in *Arabidopsis*. Plant J. 40, 200-212.

Song, J.T., Lu, H., and Greenberg, J.T. (2004b). Divergent roles in *Arabidopsis thaliana* development and defense of two homologous genes, aberrant growth and death2 and AGD2-Like Defense Response Protein1, encoding novel aminotransferases. Plant Cell 16, 353-366.

Vogel-Adghough, D., Stahl, E., Návarová, H., and Zeier, J. (2013). Pipecolic acid enhances resistance to bacterial infection and primes salicylic acid and nicotine accumulation in tobacco. Plant Sig Behav 8: e26366.

Oliver Brücher et al: "tert-Butyl 1-hydroxypiperidine-2-carboxylate", Acta Crystallographica Section E Structure Reports Online, vol. 67, No. 8, Aug. 15, 2011, pp. o2061-o2061, XP055446599.

H. T Nagasawa et al: "Synthesis of 1-hydroxy-L-proline and related cyclic N-hydroxyamino acids. Metabolic disposition of carbon-14-labeled 1-hydroxy-L-proline in rodents", Journal of Medicinal Chemistry, May 1, 1972, pp. 483-486.

Friederike Bernsdorff et al: "Pipecolic acid orchestrates plant systemic acquired resistance and defense priming via salicylic acid-dependent and independent pathways", The Plant Cell, Dec. 15, 2015.

International Search Report and Written Opinion in International Application No. PCT/EP2018/081355, dated Jan. 18, 2019.

Tortorella et al., "Zein as a versatile biopolymer: different shapes for different biomedical applications," RSC Adv., 2021, 11, 39004-39026.

* cited by examiner

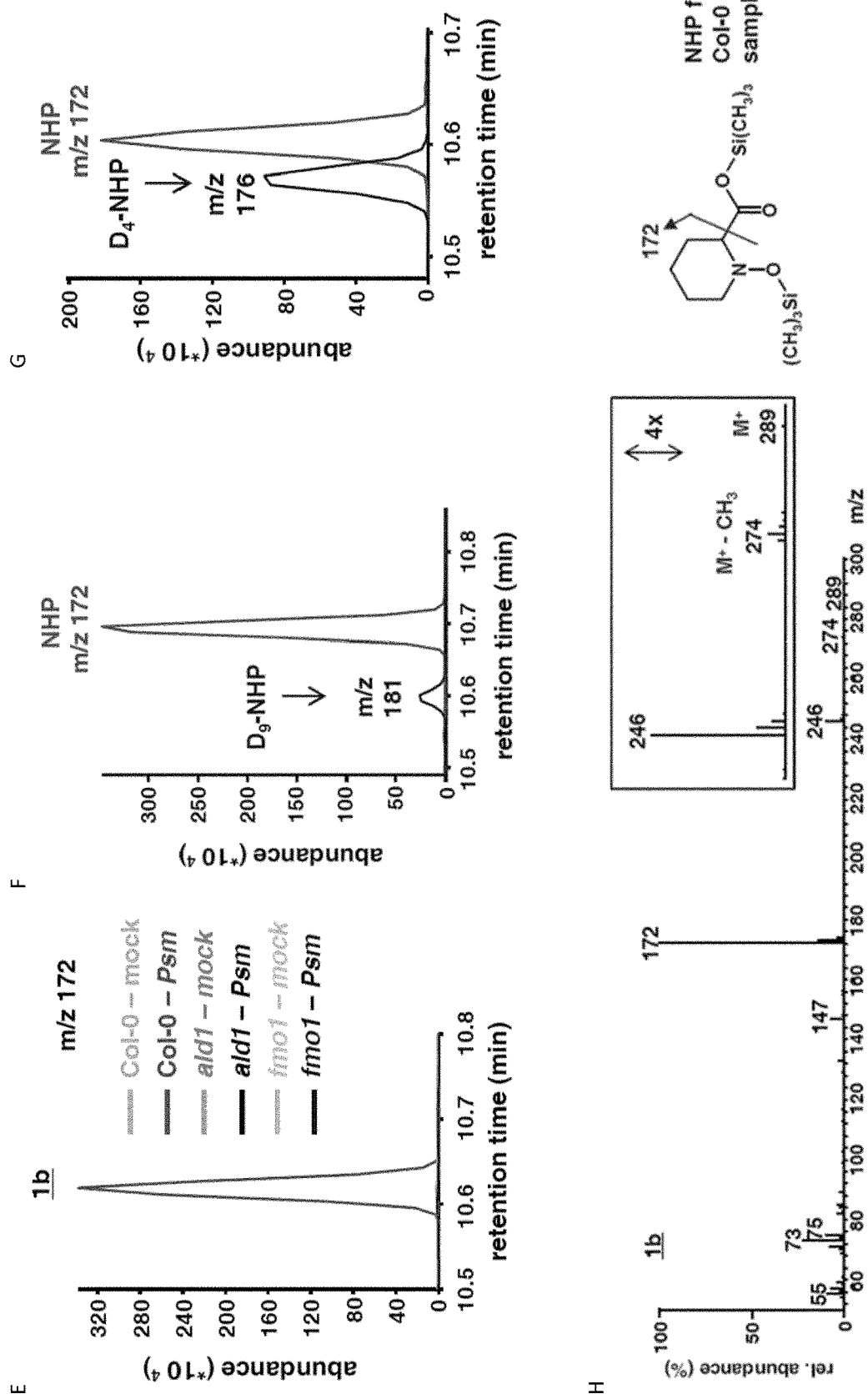
Figure 1 contin.

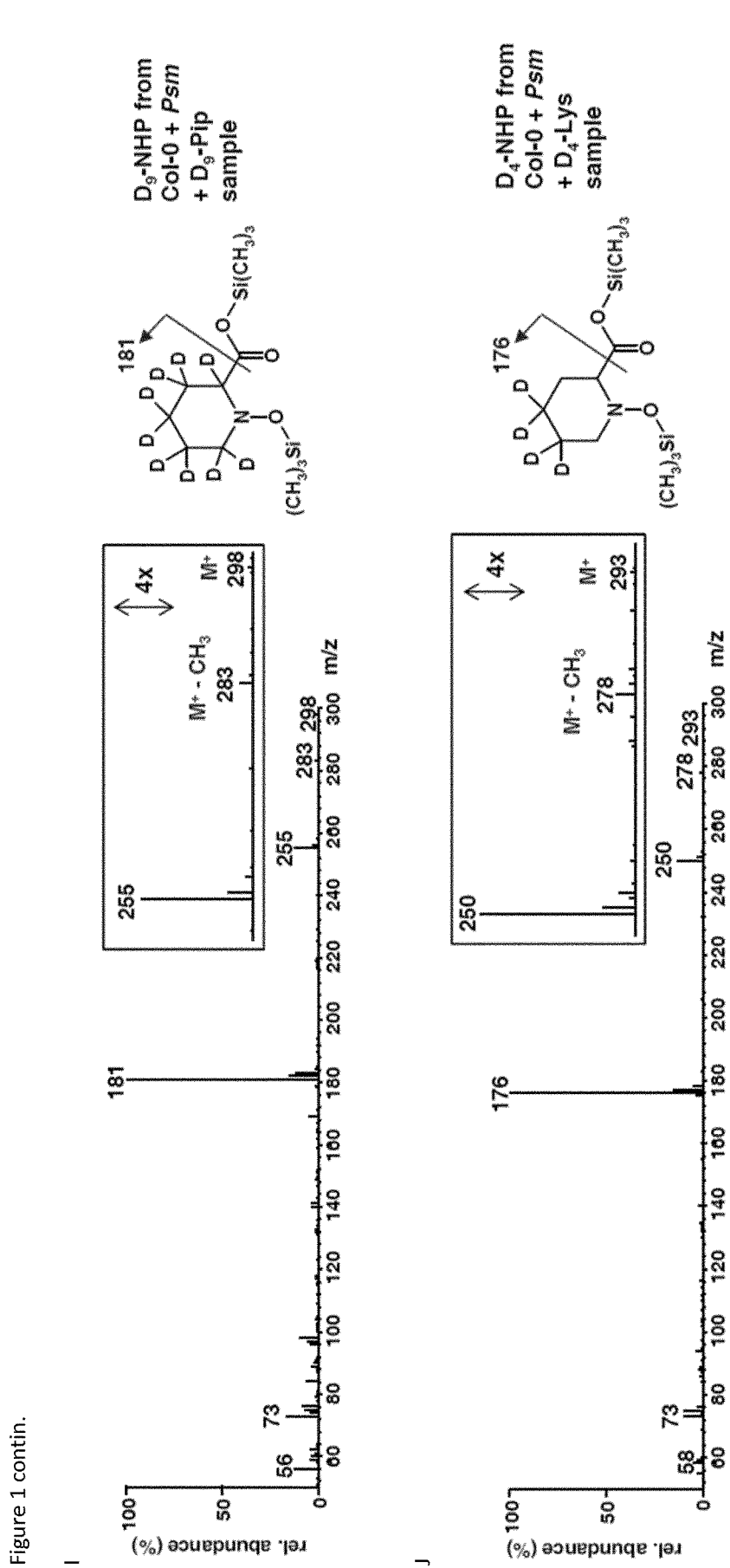
Figure 1 contin.

A

B

C

METHOD FOR INDUCING ACQUIRED RESISTANCE IN A PLANT

FIELD OF THE INVENTION

The present invention generally relates to the field of plant protection products and concerns a method for inducing acquired resistance of a plant to a plant pathogen, comprising obtaining or providing a composition comprising 1-hydroxypiperidine-2-carboxylic acid or a salt or derivative thereof, and contacting a plant with said composition, thereby inducing acquired resistance of the plant to the plant pathogen. Further, the present invention relates to the use of 1-hydroxypiperidine-2-carboxylic acid for inducing acquired resistance of a plant to a plant pathogen. Also encompassed by the present invention are a plant seed coated with a composition comprising 1-hydroxypiperidine-2-carboxylic acid or a salt or derivative thereof, an irrigation system filled with irrigation water comprising 1-hydroxypiperidine-2-carboxylic acid or a salt or derivative thereof in a concentration of at least 0.1 mM, and a composition comprising 1-hydroxypiperidine-2-carboxylic acid or a salt or derivative thereof in a concentration of at least 0.1 mM, and a plant nutrient and/or a further plant protection product or a salt or derivative thereof.

BACKGROUND OF THE INVENTION

Plants can acquire resistance towards infection by a broad spectrum of biotrophic and hemibiotrophic phytopathogens, a defense response known as systemic acquired resistance (SAR). SAR is induced by a localized leaf inoculation and provides protection to pathogen infection in the entire foliage (Fu and Dong, 2013). Plants with activated SAR exhibit enhanced systemic expression of antimicrobial PR proteins and other augmented immune responses (Sticher et al., 1997). In addition, biologically induced SAR conditions plants to react more quickly and vigorously to subsequent pathogen attack, a phenomenon designated as defense priming (Návarová et al., 2012).

SAR establishment is controlled by immune-regulatory metabolites, and two key metabolic players in the signal transduction pathway leading to SAR are the phenolic salicylic acid (SA) and the non-protein amino acid pipecolic acid (Pip) (Vernooij et al., 1994; Návarová et al., 2012). Both metabolites accumulate in the inoculated (1°) and the distant, systemic (2°) leaf tissue (Bernsdorff et al., 2016). The stress-related biosynthesis of SA in *Arabidopsis* is derived from the shikimate pathway intermediate chorismate and requires the pathogen-inducible ISOCHORISMATE SYNTHASE1 (ICS1) gene (Nawrath and Métraux, 1999; Wildermuth et al., 2001). Accumulating SA activates and physically binds to the transcriptional co-regulator NON-EXPRESSER OF PR GENES1 (NPR1) to induce plant pathogen resistance (Mou et al., 2003; Wu et al., 2012).

It has been known since the 1950s that L-pipecolic acid (Pip; (S)-piperidine-2-carboxylic acid) is widely distributed in angiosperms (Morrison, 1953; Zacharius et al., 1954; Broquist, 1991). Pip was found to be biosynthesized to high levels in response to bacterial, fungal, or viral infection in several monocotyledonous and dicotyledonous plant species, including *Arabidopsis thaliana* (*Arabidopsis*), rice (*Oryza sativa*), potato (*Solanum tuberosum*), tobacco (*Nicotiana tabacum*), and soybean (*Glycine max*; Pálfi and Dézsi, 1968; Vogel-Adghough et al., 2013; Aliferis et al., 2014). Moreover, *Arabidopsis* plants with constitutively activated defenses and autophagy mutants that exhibit stress-related phenotypes exhibit constitutively elevated Pip levels (Návarová et al., 2012; Masclaux-Daubresse et al., 2014).

In *Arabidopsis*, Pip is synthesized by a two-step biochemical process from L-Lys (Ding et al., 2016; Hartmann et al., 2017). The aminotransferase AGD2-LIKE DEFENSE RESPONSE PROTEIN1 (ALD1) catalyzes the enamine 2,3-dehydropipecolic acid (2,3-DP). 2,3-DP is subsequently reduced to Pip by action of SAR-DEFICIENT4 (SARD4) and an additional reductive activity (Hartmann et al., 2017). The SAR-essential genes ALD1 and SARD4 are systemically up-regulated in the foliage of pathogen-inoculated plants (Song et al., 2004a; Zeier, 2013; Hartmann et al., 2017). The resulting accumulation of Pip in the leaves is necessary for SAR induction and the establishment of a conditioned state which primes plants for enhanced defence activation in response to subsequent attack (Návarová et al., 2012). Pip triggers SAR and realizes defence priming by a major, SA-dependent and a minor, SA-independent signalling mode (Bernsdorff et al., 2016). Notably, the induction of acquired resistance and priming by Pip requires functional FLAVIN-DEPENDENT-MONOOXYGENASE1 (FMO1), a highly pathogen-inducible plant defense gene. This indicates that FMO1 is a critical downstream component in the Pip resistance pathway (Návarová et al., 2012; Zeier, 2013; Bernsdorff et al., 2016). Exogenously applied Pip increases the resistance of *Arabidopsis* and tobacco plants to infection with the bacterial pathogen *Pseudomonas syringae* and primes plants for early SA accumulation (Návarová et al., 2012; Vogel-Adghough et al., 2013). Furthermore, transgenic rice plants overexpressing the Pip biosynthesis gene ALD1 exhibited increased resistance toward infection by the fungus *Magnaporthe oryzae* (Jung et al., 2016). Together, these findings suggest a conserved regulatory role for Pip in plant immunity.

The genome of *Arabidopsis* contains 29 genes coding for proteins with significant sequence similarity to human flavin containing monooxygenases (FMOs; Schlaich, 2007). Based on their nucleotide sequence, plant FMO genes have been divided into three clades (Olszak et al., 2006; Yoshimoto et al., 2015). While the so far characterized FMOs of clade III are involved in the S-oxygenation of sulfides to sulfoxides within the biosyntheses of sulfur-containing plant secondary metabolites (Li et al., 2008; Yoshimoto et al., 2015), the clade II YUCCAs mediate the oxidative decarboxylation of indole-3-pyruvate to the plant hormone indole-3-acetic acid (Mashiguchi et al., 2011).

The clade I of plant FMOs contains only two *Arabidopsis* genes, the highly pathogen-inducible gene FLAVIN-DEPENDENT-MONOOXYGENASE1 (FMO1) and a pseudogene (Olszak et al., 2006; Schlaich, 2007). In 2006, three independent studies provided complementary evidence that FMO1 holds an important function in *Arabidopsis* immunity to microbial pathogen invasion (Bartsch et al., 2006; Koch et al., 2006; Mishina and Zeier, 2006). Upon inoculation with pathogens, the expression of FMO1 is systemically induced in the plant foliage and positively regulated by two key regulators of plant basal immunity, ENHANCED DISEASE SUSCEPTIBILITY1 (EDS1) and PHYTOALEXINDEFICIENT4 (PAD4) (Bartsch et al., 2006; Mishina and Zeier, 2006). An intact FMO1 gene is required for proper basal plant immunity to virulent isolates of the oomycete *Hyaloperonospora arabidopsidis* (Hpa), the causal agent of downy mildew, and to compatible strains of *P. syringae*. Consistently, overexpression of FMO1 in transgenic *Arabidopsis* enhances resistance to virulent Hpa and *P. syringae* isolates. In addition, fmo1 knockout mutants exhibit compromised specific immunity to adapted pathogens that is triggered by the TIR-NB-LRR subclass of plant resistance (R) genes (Bartsch et al., 2006; Koch et al., 2006). Moreover, functional FMO1 proved indispensable for the induction of systemic acquired resistance (SAR) (Mishina and Zeier, 2006), an inducible immune response of plants that is triggered by a localized pathogen inoculation and provides broad-spectrum resistance in the entire foliage to future attack (Shah and Zeier, 2013; Fu and Dong, 2013). A SAR-inducing 1° inoculation of a plant leaf triggers a strong transcriptional and metabolic response in non-inoculated distant (2°) leaves, and FMO1 is essential for this systemic reprogramming (Gruner et al., 2013; Bernsdorff et al., 2016).

EP 2 187 736 B1 discloses a method of priming a plant to induce a resistance response against a pathogen, the method comprising contacting a plant with a composition comprising azelaic acid or a salt thereof.

US 20160037741 discloses a method for modulating disease resistance in plants, said method comprising contacting said plant or plant part with an effective amount of at least one ascaroside, said ascaroside increasing plant resistance to one or more pathogens, and/or inducing or priming one or more plant defense responses, which are effective to inhibit pathogen growth and/or infestation.

Murahashi and Shiota (1987) describe the synthesis of NHP.

Advantageously, it was shown in the context of the present invention that elevated Pip is sufficient to induce SAR-like transcriptional reprogramming in *Arabidopsis*, a response that completely depends on FMO1. Remarkably, the biochemical function of FMO1 was identified as pipecolate N-hydroxylase which catalyses the biosynthesis of N-hydroxypipecolic acid (1-hydroxypiperidine-2-carboxylic acid) from Pip. N-hydroxypipecolic acid (NHP) accumulates systemically in the *Arabidopsis* foliage in an FMO1-dependent manner (Hartmann et al., 2018).

Advantageously, exogenous application of NHP effectively protects plants from infection by otherwise virulent *P. syringae* and Hpa, two pathogens with inherently different infection modes. The protective effect of NHP to oomycete infection is stronger than the effect of its biosynthetic precursor Pip. Thus, a novel pathogen-inducible L-Lys catabolic pathway in plants that generates NHP has been identified, an hitherto undescribed N-hydroxylated amino acid derivative with a central function in plant immunity and acquired resistance to pathogen infection. In contrast to Pip which has been described to have neuro-transmitter activity (Charles et al. (Neurochemical Research, Vol. 11, No. 4, 1986, pp. 521-525), there are to our knowledge no such reports for NHP.

The studies underlying the present invention demonstrate a central role for the previously undescribed, N-hydroxylated amino acid NHP in plant systemic acquired resistance to pathogen infection and promises the development of novel plant protection strategies.

BRIEF SUMMARY OF THE PRESENT INVENTION

The present invention relates to method for increasing resistance of a plant to a plant pathogen or to plant pathogens, comprising
a) obtaining or providing a composition comprising 1-hydroxypiperidine-2-carboxylic acid or a salt or derivative thereof, and
b) contacting a plant with said composition, thereby increasing resistance of the plant to the plant pathogen.

The present invention relates to method for inducing acquired resistance in a plant to a plant pathogen or to plant pathogens, comprising
a) obtaining or providing a composition comprising 1-hydroxypiperidine-2-carboxylic acid or a salt or derivative thereof, and
b) contacting a plant with said composition, thereby inducing acquired resistance of the plant to the plant pathogen or to plant pathogens.

In an embodiment of the methods of the present invention, the acquired resistance of the plant to a plant pathogen is induced by priming said plant to induce a resistance response to a plant pathogen.

In an embodiment of the method of the present invention, the plant is a monocot or dicot.

In an embodiment of the method of the present invention, the plant pathogen is a bacterium, fungus, oomycete, a nematode, or virus.

In an embodiment of the method of the present invention, the plant pathogen is a biotrophic or hemibiotrophic plant pathogen.

In an embodiment of the method of the present invention, the plant is contacted with said composition by contacting the roots of the plants with said composition. In an embodiment of the method of the present invention, the plant is contacted with said composition by contacting the shoots and leaves of the plants with said composition. Thus, the roots, shoots or leaves of the plants may be contacted with said composition.

In an embodiment of the method of the present invention, the plant is contacted with said composition at least once per month.

In an embodiment of the method of the present invention, the composition comprises 1-hydroxypiperidine-2-carboxylic acid or a salt or derivative thereof in a concentration of at least 0.1 mM.

In an embodiment of the method of the present invention, the composition further comprises at least one plant nutrient and/or at least one further plant protection product or a salt or derivative thereof.

The present invention further relates to the use of 1-hydroxypiperidine-2-carboxylic acid or a salt or derivative thereof for inducing acquired resistance of a plant to a plant pathogen.

The present invention further relates to a plant seed coated with a composition comprising 1-hydroxypiperidine-2-carboxylic acid or a salt or derivative thereof.

The present invention further relates to an irrigation system filled with irrigation water comprising 1-hydroxypiperidine-2-carboxylic acid or a salt or derivative thereof in a concentration of at least 0.1 mM.

The present invention also relates to a fertilizer comprising 1-hydroxypiperidine-2-carboxylic acid or a salt or derivative thereof in a concentration of at least 0.1 mM.

In an embodiment, said fertilizer is a nitrogen fertilizer, a phosphate fertilizer and/or a potassium fertilizer.

In an embodiment, said fertilizer is a monoammonium phosphate and/or diammonium phosphate fertilizer In an embodiment, said fertilizer is a NPK fertilizer.

Finally, the present invention relates to a composition, comprising
a) 1-hydroxypiperidine-2-carboxylic acid or a salt or derivative thereof in a concentration of at least 0.1 mM, and
b) a plant nutrient and/or a further plant protection product or a salt or derivative thereof.

In an embodiment, the composition is provided in form of a pellet or granulate material.

DETAILED SUMMARY OF THE PRESENT INVENTION—DEFINITIONS

As set forth above, the present invention relates to method for inducing acquired resistance in a plant to a plant pathogen and/or for increasing resistance of a plant to a plant pathogen, comprising
a) obtaining or providing a composition comprising 1-hydroxypiperidine-2-carboxylic acid or a salt or derivative thereof, and
b) contacting a plant with said composition, thereby inducing acquired resistance in the plant to the plant pathogen and/or increasing resistance of a plant to a plant pathogen.

The term "plant" refers to any organism, which is capable of photosynthesis. It is known that many plants comprise FMO1 homologs, i.e. homologs of the enzyme which was identified as pipecolate N-hydroxylase in the studies underlying the present invention. Examples for such plants are listed in the following table. Further, Pip, i.e. the precursor of 1-hydroxypiperidine-2-carboxylic acid, had been identified in several plants species (see following table as well, or Lawrence, J. M., and Grant, D. R. (1963) for pea, Jung, G. Y et al. (2016) for rice, Vogel-Adghough, D., Stahl, E., Návarová, H., and Zeier, J. (2013) for tobacco, Camañes, G., Scalschi, L., Vicedo, B., González-Bosch, C., and Garcia-Agustín, P. (2015) for *Solanum lycopersicon*, Aliferis, K. A., Faubert, D., and Jabaji, S. (2014) for Soybean, Chen, W., Li, X., Tian, L., Wu, P., Li, M., Jiang, H., Chen, Y., and Wu, G. (2014) for *Lotus japonicus*, a model organism for legumes, Zacharius, R. M. (1954) for beans (*Phascolus vulgaris*), Moulin, M. (2006) for rapeseed, Kiyota, E., Pena, I. A., and Arruda, P. (2015) for maize, Morrison, R. I. (1953) for *Trifolium repens*. Biochemical Journal 53, 474-478, Garcia-Seco, D., Chiapello, M., Bracale, M., Pesce, C., Bagnaresi, P., Dubois, E., Moulin, L., Vannini, C., and Koebnik, R. (2017) for wheat. Thus, it is plausible that 1-hydroxypiperidine-2-carboxylic acid is generated throughout the plant kingdom.

TABLE A fmo1 closest homolog in various exemplary plant species.

| Plant | Scientific name | Pipecolic acid (Pip) detected | NCBI Reference Sequence for fmo1 homologs |
|---|---|---|---|
| Rice | *Oryza sativa* | Yes | XP_015629366.1 |
| Tobacco | *Nicotiana tabacum* | Yes | XP_016452604.1 |
| Tomato | *Solanum lycopersicum* | Yes | XP_004243918.1 |
| Wheat | *Triticum aestivum* | Yes | CDM80552.1 |
| Soy bean | *Glycine max* | Yes | XP 003541317.1 |
| Rapeseed | *Brassica napus* | yes | XP_013693788.1 |
| Potato | *Solanum tuberosum* | yes | XP_006353775.1 |
| Bean | *Phaseolus vulgaris* | yes | XP_007154552.1 |
| Maize | *Zea mays* | yes | XP_008660479.1 |
| Apple | *pyrus malus* | yes | XP_008337882.1 |
| Barley | *Hordeum vulgare* L. | yes | BAK04748.1 |

In an embodiment, the plant is a plant as listed in the above table. However, the term "plant" is not limited to these plants. Accordingly, encompassed within the scope of the term "plant" are all genera and species of higher and lower plants of the Plant Kingdom. Annual, perennial, monocotyledonous and dicotyledonous plants and gymnosperms are preferred. The class of plants that can be used in the method of the invention is generally as broad as the class of higher and lower plants amenable to transformation techniques, including angiosperms (monocotyledonous and dicotyledonous plants), gymnosperms, ferns, and multicellular algae. Accordingly, the plant is preferably, a moncot plant or a dicot plant. It includes plants of a variety of ploidy levels, including aneuploid, polyploid, diploid, haploid and hemizygous. Preferred are plants and plant materials of the following plant families. Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae. Annual, perennial, monocotyledonous and dicotyledonous plants are preferred plants. Said plants may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophyceae, Rhodophyceae, Myxophyceae, Xanthophyceae, Bacillariophyceae (diatoms) and Euglenophyceae. Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, lridaceae such as gladioli, iris, freesia and crocus, Compositae such as marigold, Geraniaceae such as geraniums, Liliaceae such as Drachaena, Moraceae such as ficus, Araceae such as philodendron and many others. The plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. dulce (celery)) and many others; the family of the Solanaceae, particularly the genus Lycopersicon, very particularly the species *esculentum* (tomato) and the genus *Solanum*, very particularly the species *tuberosum* (potato) and *melongena* (aubergine), tobacco and many others; and the genus *Capsicum*, very particularly the species annum (pepper) and many others; the family of the Leguminosae, particularly the genus *Glycine*, very particularly the species max (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others. The plants according to the invention are selected in particular among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, *papaya*, mango, and other woody species including coniferous and deciduous trees such as poplar, pine, *sequoia*, cedar, oak, etc. Especially preferred plants are *Arabidopsis thaliana, Nicotiana tabacum*, oilseed rape, soybean, corn (maize), rice wheat, linseed, potato and *tagetes*. For example, the plant thus may be a soybean plant. In some embodiments, the plant may be a tobacco plant. In some embodiments, the plant may be a tomato plant. In some embodiments, the plant may be a barley plant. In some embodiments, the plant is a sugar beet plant.

In the context of the method of the present invention, it is envisaged that the plant to be contacted with the composition is grown in a greenhouse or, in particular, on a field. Thus, the plant is preferably a greenhouse-grown or field grown plant. The plant can be contacted with the composition as referred to herein at any stage after germination. E.g., it is envisaged to contact said plant with said composition post-emergence. Of course, the composition might be also applied at later stages.

In accordance with the present invention, the resistance of a plant shall be increased to plant pathogens, i.e. acquired resistance shall be induced, by contacting the plant with a composition as defined herein. Preferably, the resistance of a plant to plant pathogens is increased as compared to a plant which has not been contacted with said composition. In particular, the resistance of the plant to plant pathogens is increased by priming said plant to induce a resistance response to a plant pathogen.

The studies underlying the present invention indicate that 1-hydroxypiperidine-2-carboxylic acid primes plants against plant pathogens. Priming is a process by which a plant is prepared to initiate an effective resistance response against pathogens. In particular, the compound has been shown to increase resistance, i.e. protection, of a plant against a pathogen attack by activating underlying signaling mechanism of the plants, in particular without the direct induction so called pathogenesis related genes (PR genes). Thus, acquired resistance is induced in said plant. After, pathogen attack, a plant contacted with the composition shows increased resistance against pathogen infection compared to a plant that has not been contacted with said composition. The induced acquired resistance is preferably accompanied by a stronger activation of defense responses indicating that 1-hydroxypiperidine-2-carboxylic acid primes the plant's resistance response against pathogen attack. Apparently, 1-hydroxypiperidine-2-carboxylic acid does not consume much energy of the plant.

The composition as defined herein is preferably contacted with a plant prior to a pathogen attack. Accordingly, the plant is not infected with a pathogen at the time of the contacting with the composition. However, it is also envisaged that the plant is contacted with composition during a pathogen attack.

Generally, 1-hydroxypiperidine-2-carboxylic acid is the active ingredient in the composition that increases resistance of the plant to a plant pathogen (and thus induces acquired resistance in said plant). 1-hydroxypiperidine-2-carboxylic acid is well known in the art. It has been shown in the studies underlying the present invention, that that 1-hydroxypiperidine-2-carboxylic acid is synthesized in plants by the conversion of Pip which is catalyzed by pipecolate N-hydroxylase (FMO1 in *Arabidopsis thaliana*). 1-hydroxypiperidine-2-carboxylic acid can be also synthesized as described in the Examples section based on the protocol provided by Murahashi and Shiota (1987). 1-hydroxypiperidine-2-carboxylic acid is also referred to as N-hydroxypipecolic acid (abbreviated "NHP") herein. Further, it is referred to as 1-Hydroxypipecolic acid. The CAS number of this substance is CAS No.: 115819-92-6.

The term "or a salt thereof" typically refers to ion pairs and salts, in particular salts, which have the same or essentially the same biological activity, i.e. which are capable of inducing acquired resistance of a plant to a pathogen as referred to herein. Suitable 1-hydroxypiperidine-2-carboxylic acid salts and ion pairs are preferably water-soluble. Such salts include salts form with inorganic or organic cations, including surfactant type cations.

Examples of such cations are ammonium or alkali metal cations, such as Na+, K+ or e.g. cholinium cation or tretrabutylammonium cation. Preferred examples of 1-hydroxypiperidine-2-carboxylic acid salts include sodium and potassium salts.

The term "derivatives thereof" refers in particular to esters and amides of the respective compound, which preferably have the same or essentially the same biological activity "1-hydroxypiperidine-2-carboxylic acid" and "NHP". Preferably, pipecolic acid (Pip) is not a derivative of 1-hydroxypiperidine-2-carboxylic acid.

It is to be understood that the term ""NHP" as used within the present invention also encompasses ion pairs and salts, in particular salts, thereof, in particular salts thereof which have the same or essentially the same biological activity, i.e. which are capable of inducing acquired resistance of a plant to a pathogen as referred to herein. Further, the term "NHP" also encompasses derivatives thereof, in particular esters and amides thereof, which preferably have the same or essentially the same biological activity "1-hydroxypiperidine-2-carboxylic acid" and "NHP". Preferably, pipecolic acid (Pip) is not a derivative of 1-hydroxypiperidine-2-carboxylic acid.

In the studies underlying the present invention, a mixture of the D- and L-form of N-hydroxypipecolic acid was tested and shown to be functional. Experimental data with Pip, the precursor of NHP, have shown that L-Pip is a functional stereoisomer (Návarová et al., 2012). This is consistent with the detection of the naturally occurring L-Pip enantiomer in plants (Zacharius et al., 1954). Further, it appears to be plausible that the FMO1-mediated hydroxylation of L-Pip might proceed via the retention of the given stereochemistry. Accordingly, the term "1-hydroxypiperidine-2-carboxylic acid" as used herein preferably refers to the L-enantiomer of 1-hydroxypiperidine-2-carboxylic acid (and of NHP and 1-Hydroxypipecolic acid, respectively). Thus, the preferred NHP is L-NHP. However, the term may also refer to the D-enantiomer of 1-hydroxypiperidine-2-carboxylic acid, or to a combination of the D-enantiomer or L-enantiomer.

The preferred amount or concentration of 1-hydroxypiperidine-2-carboxylic acid or its salt or derivative thereof is an "effective amount" or "effective concentration". Accordingly, the composition as set forth in context of the present invention, comprises an effective amount or effective concentration 1-hydroxypiperidine-2-carboxylic acid. It is to be understood that an effective amount of said composition is applied. By "effective amount" and "effective concentration" is intended an amount and a concentration, respectively, that is sufficient to e.g. increased resistance of the plant to a plant pathogen, in particular to induce acquired resistance in said plant. Such an amount can be easily determined using methods known in the art. Preferably, said composition comprises 1-hydroxypiperidine-2-carboxylic acid in a concentration of at least 0.05 mM, more preferably in a concentration of at least 0.1 mM, even more preferably of at least 0.5 mM, and most preferably of at least 1 mM. Preferably, at least 10 ml of the composition are applied to a plant.

Alternatively or additionally, an effective amount of 1-hydroxypiperidine-2-carboxylic acid or of its salt or derivative thereof is about 0.01 to 10 kg/ha. Preferably, an effective amount is an amount of at least 0.5 kg/ha, more preferably an amount of at least 1 kg/ha, even more preferably and amount of at least 2 kg/ha, and most preferably an amount of at least 4 kg/ha. Accordingly, it is envisaged that the aforementioned amounts are applied per ha. The amounts however might vary considerably, and so the quantities given must be understood as being only suggestive. All amounts that operate in the manner that they increase the resistance of a plant to a pathogen fall within the scope of the invention (i.e. that they induce acquired resistance).

Alternatively or additionally, an effective amount of 1-hydroxypiperidine-2-carboxylic acid or of its salt or derivative is an amount of preferably, 0.1 µmol, more preferably, of at least 1 µmol, even more preferably of at least 5 µmol, and most preferably of at least 10 µmol of said compound per plant.

The activity of the composition as set forth in connection with the methods of the present invention is exhibited when the composition is contacted with the plant. The effect observed may depend on the stage of growth of the plant, the application parameters of dilution, the specific adjuvants and carriers employed, and the like, as well as the amount of the compounds applied. These and other factors can be adjusted as it is known in the art to promote the increase of resistance of the plant to the plant pathogen. Preferably, the composition is applied by contacting the plant or part thereof with the composition.

Preferably, the composition to be applied in the methods of the present invention is a liquid composition. More preferably, the 1-hydroxypiperidine-2-carboxylic acid or a salt thereof is solved in the composition. Accordingly, the liquid composition is preferably aqueous. The composition usually contains more than 5 wt % of water, preferably more than 10 wt %, more preferably more than 20 wt %, even more preferably more than 50 wt % of water, and most preferably more than 80 wt % of water.

Preferably, the plant is contacted with the composition at set forth herein at least once per month, more preferably, at least twice a month, and most preferably at least once a week.

Contacting the plant with the composition described herein may be carried out by any method deemed appropriate such as by watering, immersion, and/or spraying. In the case of seeds, the seeds may be also contacted with said composition by applying one or more coats comprising an effective amount of 1-hydroxypiperidine-2-carboxylic acid or a salt thereof. Accordingly, the term "contacting" as used herein relates to any suitable administration of said compound, in particular spraying, infiltrating or root watering.

In a preferred embodiment of the present invention, the plant is contacted with said composition by contacting the roots of the plants with said composition. Preferably, this is achieved by root watering, in particular by watering the plant with the composition as defined herein. Alternatively, the shoots or leaves of the plant may be contacted with the composition.

In another preferred embodiment of the present invention, the plant is contacted with said composition by spraying said composition onto the plant. In some embodiments, the composition is sprayed on the leaves of the plant, preferably in combination with a surfactant such as Silwet L-77, Tween 20, Activator 90, Ortho X-77 or Triton AG-98 for better foliar absorption. Thus, the composition as set forth herein may further comprise a surfactant. S Thus, the composition as set forth herein may further comprise a surfactant, Silwet L-77, Tween 20, Activator 90, Ortho X-77 or Triton AG-98. The aforementioned surfactants are commercially available (Activator 90 (O. 125%, Loveland Ind., Greeley, Colo.), Ortho X-77 (0.0625%, Chevron Chemical, San Francisco), Regulaid (0.25%, Kalo Laboratories, Kansas City, Me.), Silwet L-77 (0.1%, Union Carbide, Tarrytown, N.Y.), Triton AG-98 (0.0625%, Rohm and Haas, Philadelphia), and Tween 20 (0.125%, ICI Americas, Wilmington, Del.).

It is to be understood, that the composition is exogenously applied to (i.e. contacted with) the plant. The term "exogenous" as used herein with reference the composition or the 1-hydroxypiperidine-2-carboxylic acid preferably means that it does not originate from the plant (plants) that is (are) contacted with the composition. Thus, the endogenous production of the composition or the 1-hydroxypiperidine-2-carboxylic acid with the plant is not encompassed by the present invention. Thus, the composition is preferably an isolated or artificial composition rather than a plant extract.

The term "plant pathogen" is well understood by the skilled person. As used herein, the term preferably refers to an organism that can infect and cause harm to a plant. Preferably, the plant pathogen is a bacterium, fungus, oomycete, virus, or nematode. In accordance with the present invention the acquired resistance of a plants towards plant pathogens in general shall be induced, i.e. resistance of a plant to plant pathogens shall be increased. The plant pathogens are preferably pathogens selected from the group consisting of bacteria, fungi, oomycetes, viruses, or nematodes.

In a preferred embodiment, the plant pathogen is a bacterium. E.g., the plant pathogen is *Pseudomonas syringae*, such as *Pseudomonas syringae* pv maculicola ES4326 (Psm). *Pseudomonas syringae* is Gram-negative bacterium. As a plant pathogen, it is known to infect a wide range of species, and exists as over 50 different pathovars. The pathovars are well known in the art and are available from international culture collections. Other bacterial plant pathogens are *Xanthomonas* or *Erwinia* such as *Erwinia carotovora*, *Ralstonia*, or *Clavibacter*.

In another preferred embodiment, the plant pathogen is an oomycete or a fungus such as *Phytophthora*, *Fusarium* spp., *Cladosporium*, or *Erysiphe*. E.g., the plant pathogen is the oomycete *Hyaloperonospora arabidopsidis* (Hpa) is the causal agent of downey mildew in the model plant *Arabidopsis* and has been extensively studied in the context of host/pathogen co-evolution.

In another preferred embodiment, the plant pathogen is a virus such as Soybean or tobacco mosaic virus, Tobacco Ring spot virus, Tobacco Streak virus, or Tomato spotted wilt virus.

Preferred plant pathogens are disclosed in the following table with the title "plant pathogens". The table lists also potential hosts of the plant.

Thus, the plant pathogen is preferably selected from the group consisting of *Pseudomonas syringae*, *Phytophtera infestans*, *Puccinia graminis*, *Botrytis cinera* (a nectrotrophic pathogen), and *Magnaporthe oryzae*. Also preferably, the plant pathogen may be selected from the group consisting of Tobacco mosaic virus (TMV), *Oidium neolycopersici* (the causative agent of tomato powdery mildew), *Xanthomonas translucens*, and *Rhizoctonia solani*.

In another preferred embodiment, the plant pathogen is a nematode such as *Meloidogyne* spp or *Meloidogyne incognita*. *M. incognita* has a worldwide occurrence numerous hosts.

Other plant pathogens are e.g. Beet Curly Top Virus (BCTV), *Rhizoctonia solani*, and *Cercospora beticola* which are known to be sugar beet pathogens.

It is known in the art that SAR predominantly acts on biotrophic and hemibiotrophic plant pathogens. Thus, a preferred embodiment, the plant pathogen is a biotrophic plant pathogen. In an alternative preferred embodiment, said plant pathogen is a hemibiotrophic plant pathogen. Preferably, a biotrophic plant pathogen is a plant pathogen that obtains its nutrient supply only from living tissue of the infected plant. Preferably, a hemibiotrophic plant pathogen is a plant pathogen that initially invades a plant in a biotrophic mode, but later switches to a necrotrophic mode. Preferred biotrophic an hemibiotrophic organisms are disclosed in the below table.

Further, the pathogen may be a necrotrophic pathogen such as *Botrytis cinerea* (grey mould). Necrotrophic infections involve active killing of host cells and feeding from dead or dying tissue remnants.

TABLE

Plant pathogens in the context of the present invention

| Plant | SN | Variety/Ecotype | Family | Pathogen | bacterial/fungal/oomycete |
|---|---|---|---|---|---|
| Tobacco | Nicotiana tabacum | Nicotiana tabacum cv Xanthi | Solanaceae | Pseudomonas syringae pv tabaci | Phylum: Proteobacteria Family: Pseudomonadaceae |
| Tomato | Solanum lycopersicum | not specified (compare list with resistent phenotypes): e.g. red setter | Solanaceae | Phytophtera infestans | Class: Oomycota Family: Pythiaceae |
| Wheat | Triticum aestivum | — | Poaceae | Puccinia graminis (f.sp. tritici) | Phylum: Basidiomycota Family: Pucciniaceae |
| Arabidopsis | Arabidopsis thaliana | Col-0 | Brassicaceae | Botrytis cinera | Phylum: Ascomycota Family: Sclerotiniaceae |
| Soy bean | Glycine max | — | Fabaceae | Pseudomonas syringae pv glycinae | Phylum: Proteobacteria Family: Pseudomonadaceae |
| Rice | Oryza sativa | — | Poaceae | Magnaporthe oryzae (KJ-105a isolate) | Phylum: Ascomycota Family: Magnaporthaceae |

| Plant | lifestyle | Disease name | other hosts | Pathogen (Alternative) |
|---|---|---|---|---|
| Tobacco | hemibiotrophic | — | | Tobacco mosaic virus (TMV) (Virus, biotrophic) |
| Tomato | hemibiotrophic (an early asymptomatic biotrophics phase and a late necrotrophic stage) | late blight | potato | Oidium neolycopersici - the causative agent of tomato powdery mildew (biotrophic pathogen) |
| Wheat | obligate biotrophic | black stem rust, wheat stem rust | | Xanthomonas translucens pv. translucens strain CFBP 2054 (hemibiotrophic) |
| Arabidopsis | necrotrophic | broad spectrum of plants hosts, e.g.-causes disease and yield losses in vine (noble rot), strawberry, tomato | e.g. wine grapes | — |
| Soy bean | hemibiotrophic | — | | Rhizoctonia solani (basidiomycete, |
| Rice | biotrophic | rice blast fungus | rice, wheat, barley, maize (Source: ZKBS - RG 1) | — |

The expression "increasing resistance of a plant to a plant pathogen" is well understood by the skilled person. Preferably, the resistance of a plant to a plant pathogen is increased as compared to a plant which has not been contacted with a composition as set forth herein. Preferably, said control plant has been grown under the same conditions as compared to the plant that has been contacted with said composition.

Preferably, the expression "increasing resistance of a plant to a plant pathogen" is interchangeably used with the expression "inducing systemic acquired resistance response of plant" or "inducing acquired resistance in a plant". Accordingly, the present invention also relates to a method for inducing systemic acquired resistance response in a plant. The expression "systemic acquired resistance" (abbreviated "SAR") or "acquired resistance" are used interchangeably herein. The expressions are well known in the art. As used herein, the expressions preferably refer to a whole-plant resistance response. When induced, SAR or acquired resistance results in resistance of the plant that is pathogen nonspecific. After induction of acquired resistance in a plant, the plant is primed (sensitized) to more quickly and more effectively activate defense response against a plant pathogen attack. SAR is important for plants to resist disease, and for recovering from infection with a plant pathogen. The resistance observed following induction of acquired resistance is effective against a wide range of pathogens. Therefore, SAR is also referred to as "broad spectrum resistance".

The composition disclosed in the context of the present may also be also administered to a plant, i.e. contacted with a plant, in combination with a plant nutrient such as nitrate, ammonium, potassium, phosphate, manganese, iron Further, the composition may be also contacted with a plant in combination with further plant protection product or salt or derivative thereof.

Accordingly, the present invention further contemplates that composition as set forth in connection with the present invention above further comprises at least one plant nutrient and/or at least one further plant protection product or salt or derivative thereof.

Said at least one plant nutrient may be a macronutrient or micronutrient. Preferably, said at least one nutrient is one or more nutrient(s) selected from the group of nutrients consisting of ammonium sulphate, calcium carbonate, calcium sulphate calcium nitrate, magnesium phosphate, magnesium sulphate, mono potassium phosphate, potassium bicarbonate, potassium nitrate, and potassium sulphate.

In particular, the composition further comprises nitrogen, phosphorus and potassium.

The present invention further relates to a fertilizer comprising 1-hydroxypiperidine-2-carboxylic acid or a salt or derivative thereof. Preferred concentrations or amounts of 1-hydroxypiperidine-2-carboxylic acid are disclosed elsewhere herein. E.g., the fertilizer comprises 1-hydroxypiperidine-2-carboxylic acid or a salt or derivative thereof in a concentration of at least 0.1 mM.

A fertilizer is preferably any material of natural or synthetic origin (other than liming materials) that is applied to soils or to plant tissues to supply one or more plant nutrients to the growth of plants. The fertilizer shall be a plant fertilizer. In an embodiment, said fertilizer is nitrogen fertilizer, a phosphate fertilizer or a potassium fertilizer. In particular, said fertilizer is a monoammonium phosphate (MAP) and/or diammonium phosphate (DAP) fertilizer. Further, the fertilizer may be a NPK fertilizer, i.e. a fertilizer comprising at least nitrogen (N), phosphorus (P) and potassium (K), in particular in agriculturally acceptable amounts.

In an embodiment, the composition or fertilizer of the present invention is provided in form of a pellet or granulate material.

The definitions and explanations given herein above preferably apply mutatis mutandis to the following.

The present invention also relates to the use of 1-hydroxypiperidine-2-carboxylic acid or a salt or derivative thereof for increasing resistance of a plant to a plant pathogen. The present invention further relates to the use of 1-hydroxypiperidine-2-carboxylic acid or a salt or derivative thereof for inducing acquired resistance in a plant. The present invention also relates to the use of 1-hydroxypiperidine-2-carboxylic acid or a salt or derivative thereof as plant protection product.

In particular, the present invention also relates to the use of a composition comprising 1-hydroxypiperidine-2-carboxylic acid or a salt or derivative thereof (as defined elsewhere herein) for a) for increasing resistance of a plant to a plant pathogen, b) inducing acquired resistance of a plant to a plant pathogen and/or c) as plant protection product. Said composition may further comprise at least one plant nutrient and/or at least one further plant protection product.

The present invention further relates to a plant seed coated with a composition comprising 1-hydroxypiperidine-2-carboxylic acid or a salt or derivative thereof. The plant seed is preferably a seed of a plant as described above. Preferably, said seed shall comprise and an artificial coat (i.e. with a coat which is not natural with respect to said seed) comprising a composition comprising 1-hydroxypiperidine-2-carboxylic acid or a salt or derivative thereof, in particular 1-hydroxypiperidine-2-carboxylic acid or a salt or derivative thereof in a concentration as described above. Accordingly, the seed may be encapsulated with a composition comprising 1-hydroxypiperidine-2-carboxylic acid or a salt or derivative thereof (in particular, in a concentration as described above). Said composition and/or the 1-hydroxypiperidine-2-carboxylic acid or a salt or derivative thereof shall be exogeneous, i.e. heterologous with respect to the to the plant seed.

The present invention further relates to a method for the production of the plant seed of the present invention. Said method shall comprise coating a plant seed with the composition as set forth herein above in connection with the method of the present invention for inducing acquired resistance.

The present invention also relates to a plant comprising a composition set forth herein above in connection with the method of the present invention for inducing acquired resistance. Preferably, said composition is an exogenous composition. Preferably, the plant comprises the composition on its surface, i.e. on parts of the surface. More preferably, the plant comprises the composition on the roots, i.e. on the surface or part of the surface of the roots. In some embodiments, the plant comprises the composition on the leaves, i.e. on the surface or part of the surface of the leaves. In some embodiments, the plant comprises the composition on the shoot, i.e. on the surface or part of the surface of the shoot.

Further, the present invention relates to an irrigation system filled with irrigation water comprising 1-hydroxypiperidine-2-carboxylic acid or a salt or derivative thereof in a concentration of at least 0.1 mM. Preferably, said irrigation system comprises, i.e. is filled with, more than 500 l, more preferably, more than 1000 l, and more preferably more than 2000 of water comprising 1-hydroxypiperidine-2-carboxylic acid or a salt or derivative thereof in a concentration of at least 0.1 mM. Further, preferred concentrations are disclosed above.

Preferably, the term "irrigation system" as used herein refers to an assembly of component parts that is permanently installed for the controlled distribution of water to irrigate plants. Accordingly, the irrigation system shall allow the watering of the plants.

In a preferred embodiment, the irrigation system is a sprinkler irrigation system or a center pivot irrigation system.

Finally, the present invention relates to a composition comprising
a) 1-hydroxypiperidine-2-carboxylic acid or a salt or derivative thereof in a concentration of at least 0.1 mM, and
b) a plant nutrient and/or a further plant protection product or a salt or derivative thereof.

The Figures show:

FIG. 1. FMO1 functions as a Pip N-hydroxylase and catalyzes N-hydroxy-Pip formation in vivo and in vitro (A) N-hydroxy-Pip (NHP) accumulates in wild-type Col-0 plants but not in ald1 and fmo1 after *P. syringae* inoculation. Segment of overlaid ion chromatograms (m/z=100) of GC-MS-analysed extract samples from mock-treated or Psm-inoculated leaves (48 hpi) of Col-0, ald1, and fmo1 plants after sample derivatisation by methylation. The molecular species 1a is exclusively present in the Col-0-Psm samples (green).

(B) Biochemical in vitro assays with recombinant FMO1, as analysed by GC-MS after analyte derivatisation by methylation. Segments of overlaid ion chromatograms (m/z=100) are shown. Substance 1a is detected as the reaction product in full enzyme assays containing 50 μg ml$^{-1}$ FMO1, 200 μM FAD$^+$, 400 μM NADH, and 10 mM L-Pip as the substrate (blue). 1a is not detected in control assays lacking either L-Pip (red), FMO1 protein (black), FAD$^+$ cofactor (green), or NADH (brown).

(C) Mass spectrum of 1a from Col-0 extract samples, which is identical to the spectra recorded from samples of the enzymatically-generated substance and of chemically synthesized, authentic N-hydroxy-Pip (Figure S5). The chemical structure of methylated (derivatised) NHP, the molecular ion (M⁺) of m/z 159, and a plausible fragmentation that causes the dominant m/z 100 ion are indicated. The methyl group introduced by sample derivatization is indicated in blue.

(D) Infrared (IR) spectrum of 1a, as determined by GC-Fourier Transform IR spectroscopic analysis of a Col-0-Psm extract sample. Assignments of main IR bands to functional group vibrations (wavenumber/vibration): 3595 $cm^{-1}$/O—H stretching; 2952 $cm^{-1}$/C—H (methyl) stretching; 2867 and 2838 $cm^{-1}$/C—H (methylene) stretching; 1761 $cm^{-1}$/C=O stretching; 1187 $cm^{-1}$/C—O stretching.

(E) Segment of overlaid ion chromatograms (m/z=172) of GC-MS-analysed extract samples from mock-treated or Psm-inoculated leaves (48 hpi) of Col-0, ald1, and fmo1 plants after sample derivatisation by trimethylsilylation. Bis-trimethylsilylated NHP 1b is exclusively detected in the Col-0-Psm samples (green).

(F and G) NHP is biosynthetically derived from Pip and L-Lys in plants. Feeding of isotope-labelled $D_9$-Pip (F) and L-Lys-4,4,5,5-$d_4$ (G) to Psm-inoculated Col-0 plants results, in addition to natural NHP (m/z 172), in the formation of $D_9$-labelled NHP (m/z 181) (F) and $D_4$-labelled NHP (m/z 176) (G), respectively. GC-MS analyses were performed after sample derivatisation by trimethylsilylation.

(H-J) Mass spectra with indicated M⁺ ions and plausible fragmentation patterns of bistrimethylsilylated NHP (1b) (H), $D_9$-NHP (I), and $D_4$-NHP (J). The spectra are derived from the substance peaks depicted in (E), (F), and (G). Please note the shifts in the fragmentation patterns by nine (I) and four (J) mass units compared to unlabelled 1b.

Figure 2:
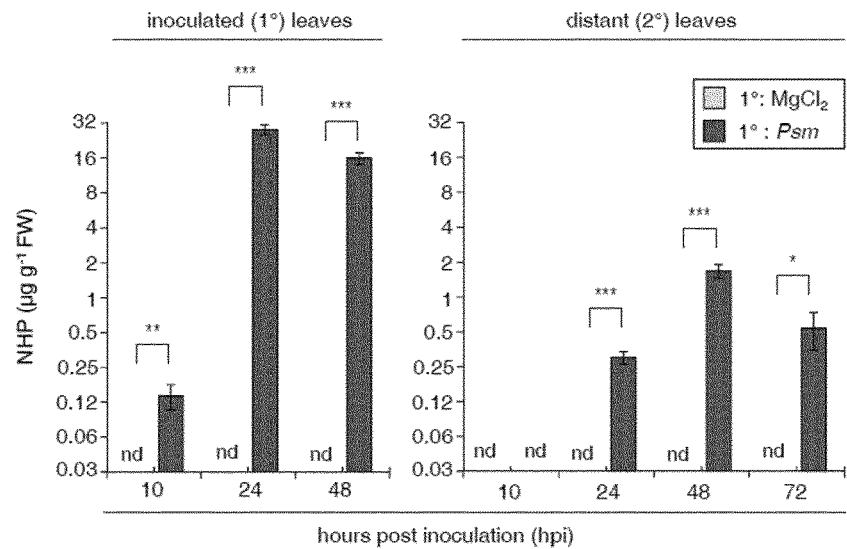
Figure 2:
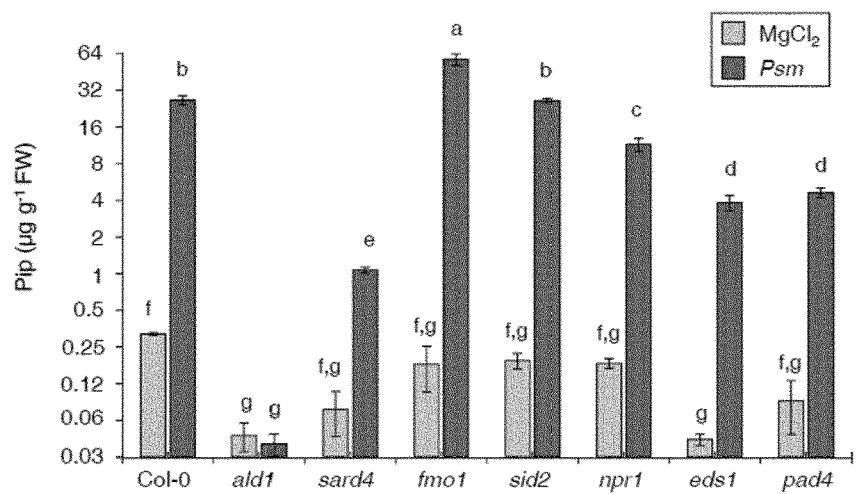
Figure 2:
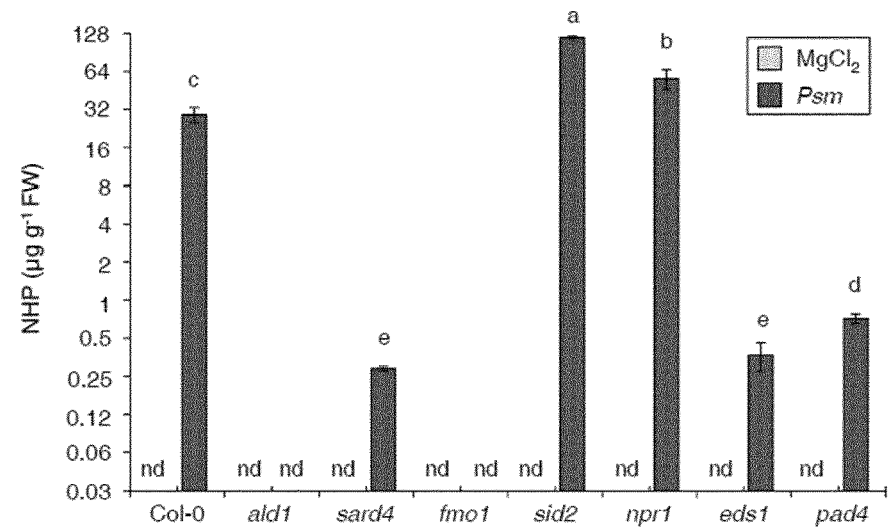

FIG. 2. NHP accumulates systemically in the *Arabidopsis* foliage at the onset of SAR (A) Levels of N-hydroxypipecolic acid [µg $g^{-1}$ leaf fresh weight (FW)] in Psm-inoculated (1°) leaves and distant (2°) leaves of Col-0 plants at different times after inoculation. 5 week-old plants were inoculated in three 1° leaves with Psm ($OD_{600\ nm}$=0.005) or infiltrated with 10 mM $MgCl_2$ (mock-treatment). Data represent the mean±SD of at least three biological replicates. Asterisks denote statistically significant differences between Psm- and mock-treated samples of a given point of time (*P<0.05; P<0.01; *P<0.001; two-tailed t test). Please note that NHP was not detected (nd) in the control samples (detection limit ~0.01 µg $g^{-1}$ FW) and that the y-axes are presented in logarithmic ($log_2$) scaling. (B and C) Levels of Pip (B) and NHP (C) in Psm-inoculated and 10 mM $MgCl_2$-infiltrated (mock-control) leaves of Col-0 and different mutant plants at 24 hpi. Data represent the mean±SD of at least three biological replicates. Different letters above the bars denote statistically significant differences (P<0.05, ANOVA and post-hoc Tukey HSD test). The y-axes have logarithmic ($log_2$) scaling.

Figure 3:
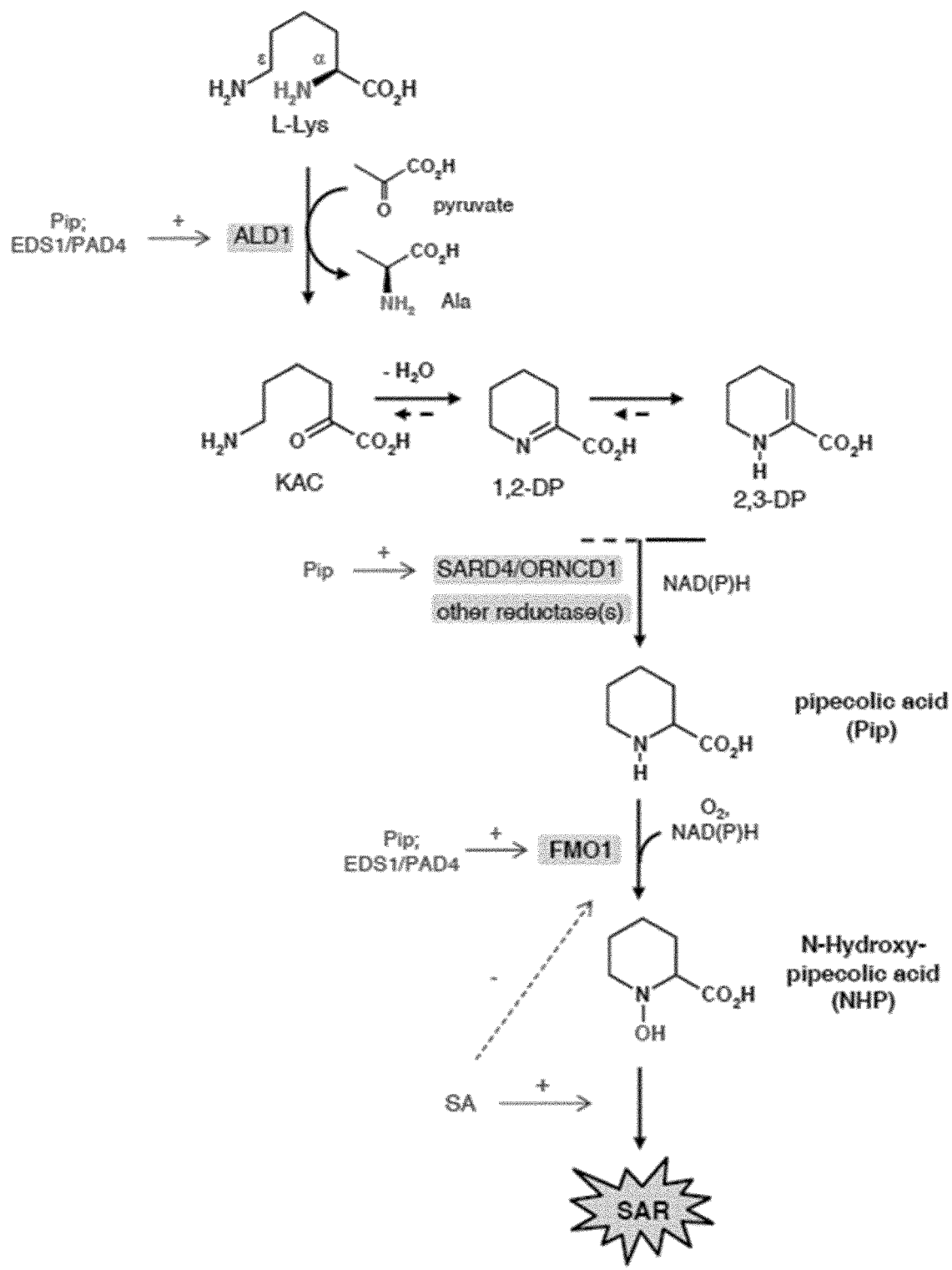

FIG. 3. The NHP biosynthetic pathway defines a novel, pathogen-inducible route of L-Lys catabolism in plants that is essential for SAR The aminotransferase ALD1 catalyses the transfer of the a-amino group of L-Lys to acceptor oxoacis such as pyruvate. The product oxoacid e-amino-a-ketocaproic acid (KAC) in turn undergoes dehydrative cyclization to 1,2-dehydroxypipecolic acid (1,2-DP) which isomerizes to the in planta detectable enamine 2,3-DP. The reductase SARD4/ORNCD1 and other reductase activities then catalyse the NAD(P)H-consuming reduction of DP intermediates to Pip. Finally, Pip is N-hydroxylated by the Flavin monooxygenase FMO1 to NHP whose accumulation is necessary for SAR. The pathway is activated at the level of transcription. ALD1, SARD4, and FMO1 transcripts systemically accumulate in the *Arabidopsis* foliage and are positively regulated by Pip and the EDS1/PAD4 defense signaling node. SA cooperates with NHP in acquired resistance induction and dampens the surplus accumulation of NHP.

Figure 4:
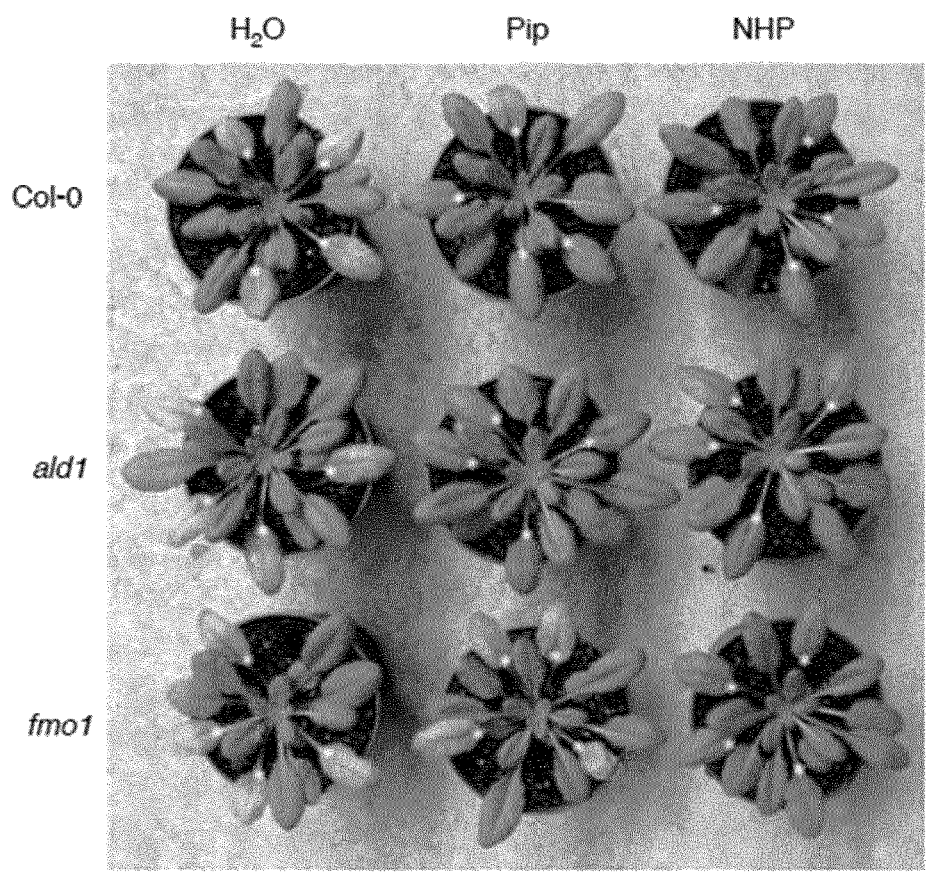
Figure 4:
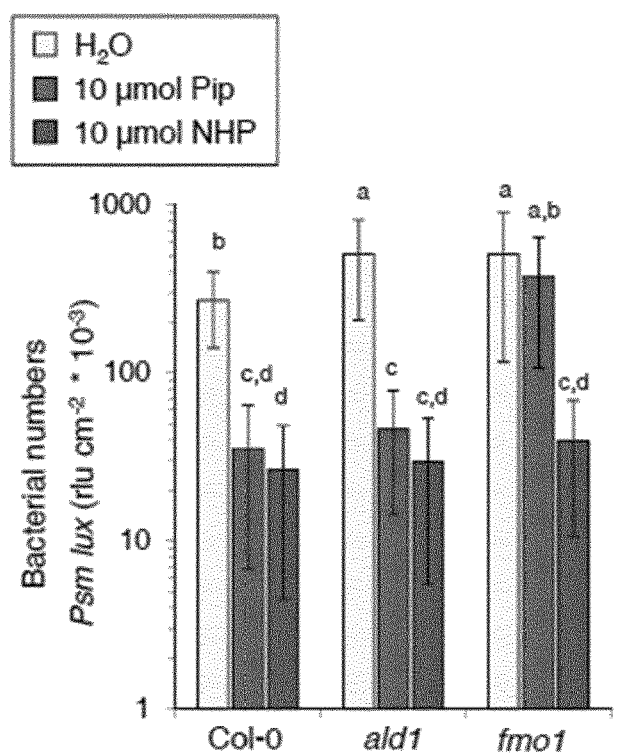
Figure 4:
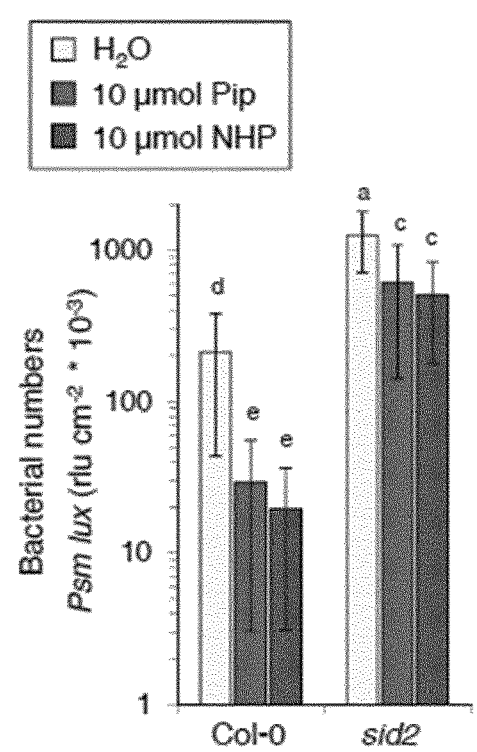

FIG. 4. Exogenous NHP is a potent inducer of *Arabidopsis* immunity to *P. syringae* infection and overrides the acquired resistance defect of the NHP-deficient fmo1 mutant (A) 5 week-old *Arabidopsis* Col-0, ald1, or fmo1 plants were pretreated with 10 ml of a 1 mM solution of Pip (middle) or NHP (right) via the soil (doses of 10 µmol per plant). Non-pretreated plants were watered with 10 ml of $H_2O$ instead (left). One day later, four leaves of each plant were inoculated with Psm lux ($OD_{600\ nm}$=0.001). Representative plants were photographed 72 h post inoculation (hpi). The pathogen-inoculated leaves are marked with white asterisks at the bases of their leaf blades.

(B and C) Bacterial numbers were assessed at 60 h post inoculation with the bioluminescent Psm lux strain by luminescence measurements and expressed as relative light units (rlu) per $cm^2$ leaf area. Data represent the mean±SD of the growth values of at least 20 leaf replicates from 6 to 7 different plants. Different letters above the bars denote statistically significant differences (P<0.005, ANOVA and post-hoc Tukey HSD test). Experiments with Col-0, ald1 and fmo1 (B) and Col-0 and sid2 (C) are shown. The results were confirmed in three independent experiments.

Figure 5:
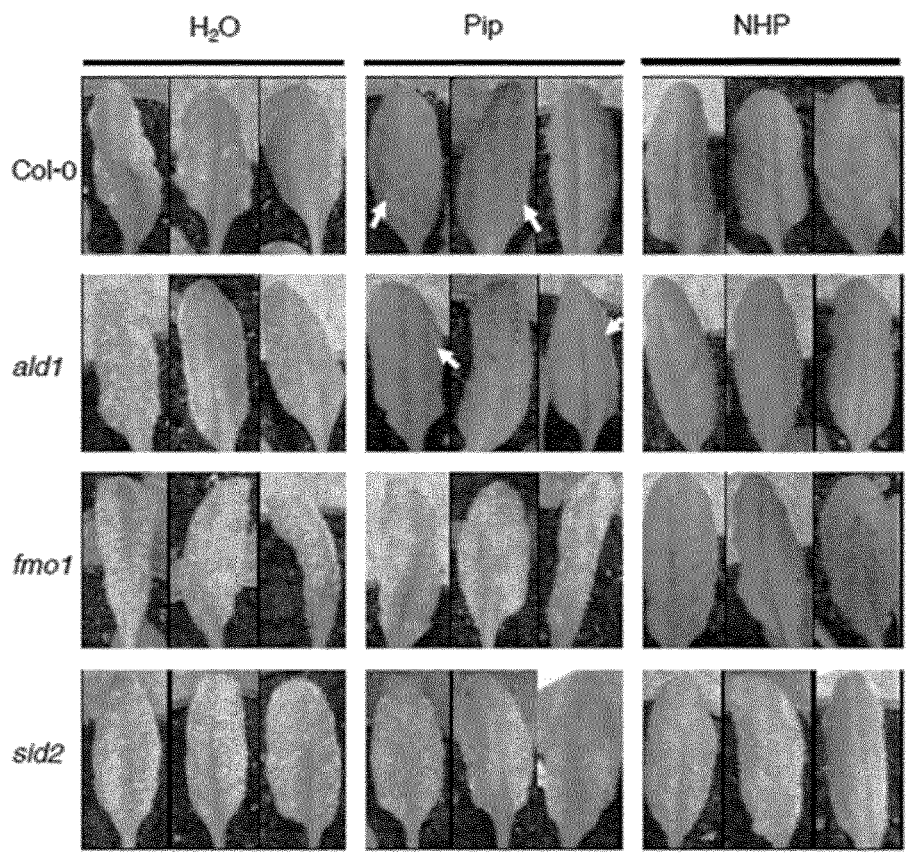
Figure 5:
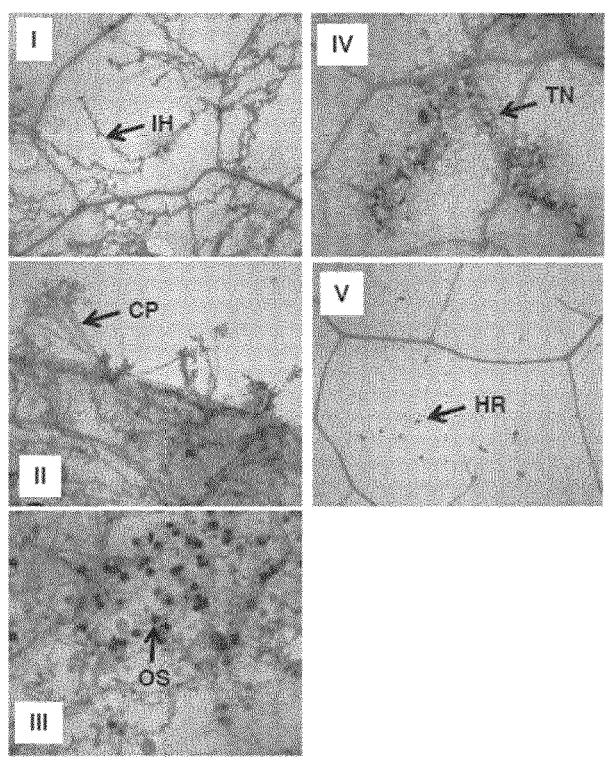

FIG. 5. Exogenous NHP effectively protects *Arabidopsis* from invasion by the oomycete *Hyaloperonospora arabidopsidis* (Hpa) and mediates, in contrast to Pip, acquired resistance to fmo1

(A) 4 week-old *Arabidopsis* Col-0, ald1, fmo1, and sid2 plants were pretreated with Pip (middle) or NHP (right) as described in FIG. 4A. Non-pretreated control plants (left) and pretreated plants were spray-inoculated with a suspension of 5*10⁴ $ml^{-1}$ conidiospores of the compatible Hpa isolate Noco2. Leaves of plants were photographed 7 days after inoculation to visualize their symptomology. 3 representative leaves for each case are depicted. Please note that NHP-pretreated Col-0, ald1, and fmo1 plants appear completely symptom-free, whereas non-pretreated plants show extensive areas of whitish downy mildew symptoms. Pip-treated Col-0 and ald1 plants only sporadically show small areas of visible mildew symptoms (arrows). Non-pretreated and Pip-pretreated fmo1 plants show similar, heavy disease symptomology.

(B) Micrographs (magnification 50-fold) of Trypan-blue-stained leaves of Hpa Noco2-inoculated *Arabidopsis* Col-0 plants at 7 dpi, representing typical disease stages (I, II, III) or resistance phenotypes (IV, V). I: free intercellular hyphae (IH) inside leaf; II: conidiophores (CPs) on leaf surface; III: area with dense oospore (OS) formation on leaf; IV: trailing necrosis (TN) of plant cells encasing hyphae; V: symptom-free leaf with sporadically occurring, highly localized hypersensitive response (HR) lesions by a single or a few plant cells.

(C) Quantitative assessment of different disease stages (IH, CP, OS) and resistance characteristics (TN) of inoculated leaves of control-, Pip-pretreated or NHP-pretreated Col-0 plants at 7 dpi. Top left: length of total intercellular hyphae (mm) per $cm^2$ leaf area. Top right: Length of intercellular hyphae associated with trailing necrosis (TN) related to the length of total (sum of free and TN-associated) intercellular hyphae (in %). Bottom left: number of conidiophores per cm² leaf area. Bottom right: number of oospores per cm² leaf area. Bars represent means±SD of 10 leaf replicates from 5 different plants.

(D) Quantitative assessment of different disease stages (IH, CP, OS) of Hpa-inoculated Col-0, ald1, fmo1, and sid2 plants in a further experiment. Bars represent means±SD of 10 to 12 leaf replicates from 5 to 6 different plants. Different letters above the bars denote statistically significant differences (P<0.05, ANOVA and post-hoc Tukey HSD test). The results were confirmed in three independent experiments.

Figure 6:
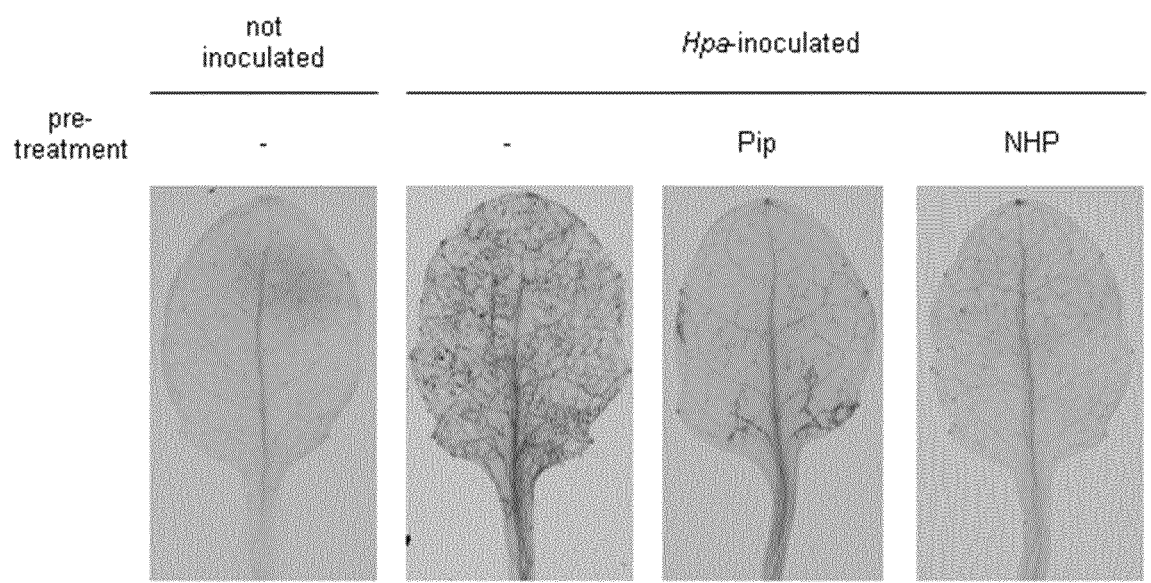

FIG. 6: Overview shots of representative Trypan-blue-stained leaves of Hpa Noco2-inoculated Arabidopsis Col-0 plants after different pre-treatments: supplementation with 10 ml H2O (–), 10 µmol Pip (Pip), or 10 µmol NHP (NHP). Leaves were harvested and stained at 7 dpi. A non-inoculated, Trypan blue-stained leaf is shown for comparison.

As can be derived from FIG. 6, there is less growth of the pathogen in the leaves of plants treated with NHP as compared to plant treated with the precursor Pip. Thus, the exogenous application of NHP allows for an improved resistance.

Figure 7:
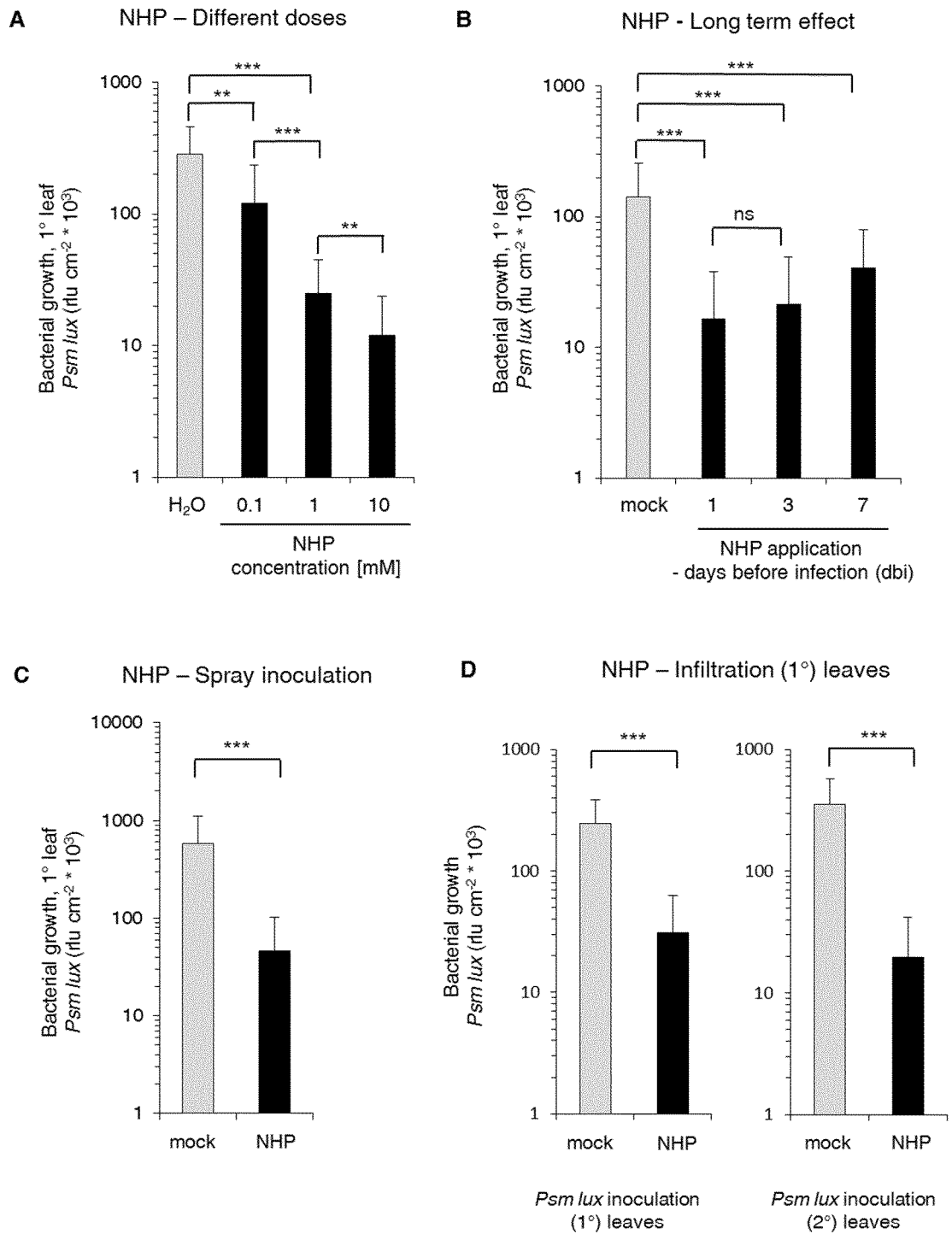

FIG. 7: Various aspects of basal resistance responses and NHP-induced resistance in wild-type Arabidopsis thaliana Col-0 plants
A. Effect of Different Doses of NHP Against *Pseudomonas syringae* in Arabidopsis thaliana Col-0 Plants.

Plant pots were supplied with 10 ml of water or 10 ml of variably concentrated NHP solutions (0.1 mM, 1 mM and 10 mM, corresponding to a total applied amount of 1, 10 and 100 µmol of NHP per pot, respectively) 24 h prior to inoculation with bioluminescent Psm lux ($OD_{600}$=0.001) to determine the efficacy of NHP at different doses. Bacterial growth was assessed 54 h later by luminescence and expressed as relative light units (rlu) per cm² leaf area. Data represent the mean±SD of the growth values of at least 8 plants with 3 leaf replicates each. The leaves of plants treated with a 1 mM solution had about 11-fold lower levels of bacteria compared to the leaves of control plants, making them largely symptom-free. At a 10-fold lower dose (1 µmol/pot) there was still a statistically significant reduction of bacterial numbers (about 2-fold). The pre-treatment with 100 µmol of NHP manifested a highly significant preventive effect against *Pseudomonas* syringae, resulting in an about 20-fold reduction as compared to mock-treated plants and thus a significant augmentation of the resistance effect compared to plants treated with 10 µmol of NHP, attested by a further 2-fold reduction of bacterial growth.
B. Preventive Effect of NHP on *Arabidopsis* Plants Inoculated at Different Time Points after Applying a Fixed Dose of 10 µMol of NHP to Individual Pots.

In this experiment, 10 ml of 1 mM solution of NHP were applied 1, 3 and 7 days before infection (dbi) with bioluminescent Psm lux (OD600=0.001) to determine how long the protective effect of NHP-treatment is lasting. Bacterial growth of treated plants was assessed 54 hours after inoculation with Psm lux as described above. Plants treated 1 d before inoculation with Psm lux showed an about 9-fold reduction in bacterial numbers in inoculated leaves as compared to mock-treated plants. After 3 days, the reduction in bacterial numbers was still highly significant at about 6-fold. Plants pre-treated 7 days before inoculation with Psm lux also showed a significant reduction in bacterial numbers in leaves (at about 3-fold).
C. Exogeneous Application of NHP Via Foliar Spray Results in a Strong Induction of *Arabidopsis thaliana* Immunity to *Pseudomonas syringae* Infection. 4 to 5-week old Col-0 plants were pre-treated 24 hours before inoculation with Psm lux by spraying a 1 mM solution of NHP or a mock solution, both supplemented with 0.005% of the surfactant Silwet 1-77, on individual *Arabidopsis* plants until the adaxial side of the leaves (upper side) was evenly covered in fine droplets of the solution. In total, 10 ml of the solution were needed to saturate the leaves of 12 plants (=1 tray) with droplets. Please note that in watering experiments the same dose is used for the treatment of one single plant (10 ml of a 1 mM NHP solution per pot; e.g. FIG. 7A). Growth of Psm lux in 1° leaves was assessed 54 h post inoculation by luminescence measurements. NHP pre-treatment by foliar spray resulted in an about 12-fold reduction of bacterial numbers in Psm lux-inoculated 1° leaves. Experimental details and statistical analyses are as described for FIG. 1A. Plants used in this experiment were 4-5-weeks old.
D. Pre-Treatment of 1° Leaves by Infiltration of a 1 mM NHP Solution Leads to a Strong Induction of Immunity to Subsequent Infection with *P. syringae* in the Local (Left) and Systemic (Right) Foliage.

5-week old plants have been pressure-infiltrated either with a 1 mM solution of NHP or respective mock solutions from the abaxial side of the leaf 24 h before inoculation of either 1° or 2°-leaves with Psm lux and assessment of bacterial growth via bioluminescence as described above. In both scenarios a strong preventive protection effect in the local as well as the systemic foliage towards subsequent Psm lux infection could be observed, resulting in an about 8-fold reduction of bacterial numbers when Psm lux was infiltrated in the pre-treated 1° leaves and a more than 15-fold reduction when 2°-leaves were inoculated. Experimental details and statistical analyses are as described for FIG. 1A. Plants used in this experiment were 4-5-weeks old.
Growth Conditions and Statistical Analysis:

All plants used in the resistance assays described in FIG. 7 have been grown under short day conditions in environmentally controlled growth chambers and were used 5-6 weeks old as described in Hartmann et al., 2018 (Cell 173, 456-469.e16) unless stated otherwise. Bars represent mean values (+SD) of at least 24 replicate samples. Asterisks denote statistically significant differences between indicated samples (*P<0.001 and P<0.01; ns, not significant; two-tailed paired student's t-test).

Figure 8:
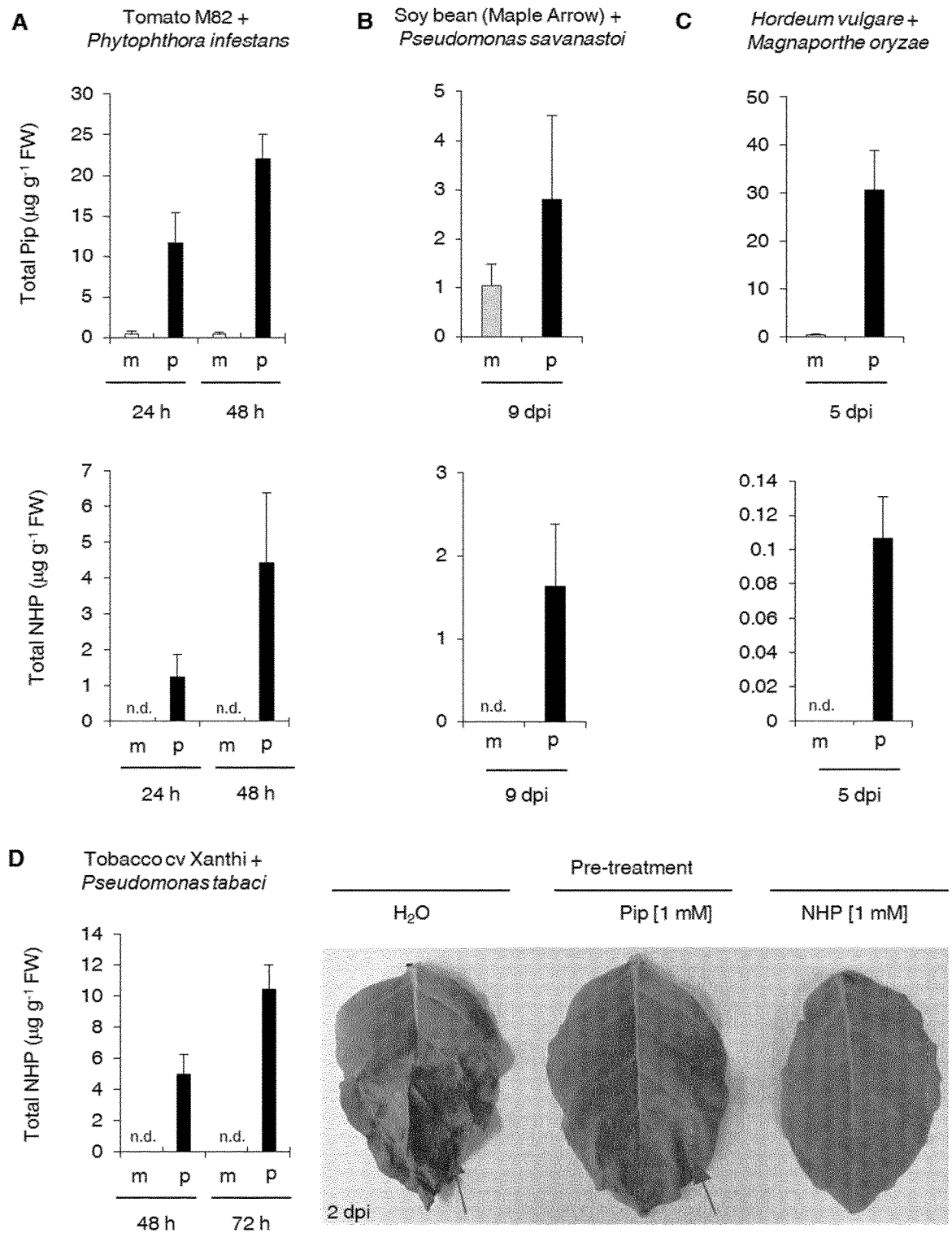

FIG. 8: Accumulation of NHP biosynthetic pathway metabolites in the course of host-pathogen-interactions in various plant species and acquired resistance in tobacco by exogenous NHP application.
A to C. Accumulation of NHP Biosynthetic Pathway Metabolites in the Course of Host-Pathogen-Interactions in Selected Monocotyledonous and Dicotyledonous Plant Species.

The accumulation of NHP and its direct biosynthetic precursor Pip was investigated in the following plant-pathogen constellations. (A) 4 week-old, MS-medium-grown tomato plants (cultivar M82) were inoculated with *Phytophthora infestans* strain D12.2 (50 spores/ml) and samples were taken at 24 h and 48 h after infection. A strong pathogen-induced accumulation of Pip (>20 µg/g fresh weight; FW) and NHP (>4 µg/g FW) could be observed in inoculated plants (p) after 48 h. Mock-treated plants (m) showed only traces of Pip and no NHP at the chosen harvest time points. (B) 3-week-old Soy bean plants (*Glycine max*: cultivar "Maple Arrow") were spray-inoculated onto the abaxial side of the first fully extended trifoliate with a suspension of *Pseudomonas syringae* subsp. *savastanoi* (DSM 50267: OD600=0.1; 0.005% Silwet 1-77) and samples were taken after first severe disease symptoms developed (9 dpi). At this distinct time point pathogen-induced Pip as well as NHP could be detected at moderate levels in Psm-inoculated plants (4 µg/g FW Pip and 1-2 µg/g FW NHP). (C) Barley (*Hordeum vulgare*) plants (3-weeks-old) inoculated with the rice blast fungus *Magnaporthe oryzae* (by foliar spray with a mock solution or a solution containing 2*10$^5$ conidiospores/ml, 2 g/l gelatin, 1 ml/l Tween) showed a strong pathogen-induced accumulation of the NHP-precursor Pip at 5 dpi, whereas mock-treated plants only showed traces of the metabolite. At this harvest point low amounts of pathogen-induced NHP could be detected. Future studies including additional plant-pathogen pairs, with an emphasis on plants with a high nutritional and economical value, will have to be conducted. Of particular interest will be the tempo-spatial accumulation of NHP in response to an individual pathogen stimulus to determine optimal pre-treatment conditions, such as the best time window and mode of application for each host-pathogen constellation. Bars represent mean values (+SD) of at least 3 replicate samples.

D. NHP Watering Confers Disease Resistance to Tobacco Plants Inoculated with *Pseudomonas tabaci*.

Left: NHP accumulates in tobacco plants (*Nicotiana tabacum* L. cv Xanthi) strongly at 48 and 72 hours after inoculation with *Pseudomonas syringae* pv. *tabaci* (DSM 1856) with peak values of approximately 10 µg/g FW after 72 h. No NHP could be detected in mock-treated plants. Right: Soil applied NHP induces resistance in tobacco plants to *Pseudomonas tabaci* infection. Plant pots with tobacco at the 4-leaf stage (BBCH growth stage 1004) were supplied with either 40 ml of H$_2$O (mock-treatment; left) or 40 ml of 1 mM Pip or NHP (=40 µmol) 1 d prior to inoculation with a suspension (OD600=0.005, O/N-culture grown at 18° C.) of *Pseudomonas tabaci* via pressure infiltration. The total dose of NHP was adjusted to compensate for the 4-5 fold bigger soil volume of the pots and the significantly higher biomass of tobacco plants at this growth stage as compared to *Arabidopsis thaliana* plants. Infiltrated 1° leaves from representative plants were cut and photographed 48 h after the initial infection. Please note the distinct disease symptoms in the water-treated control plant. The disease symptoms (arrows indicate areas of strong yellowing and wilting) are severely reduced in the Pip-pretreated plants and almost absent in NHP-pretreated plants.

Growth Conditions:

All plants used in the metabolite analyses studies have been grown under the following conditions in environmentally controlled growth chambers. Tomato plants were grown with a 12 h light and 12 h dark cycle at 23° C. (day) and 18° C. (night). Soy plants were grown with a 16 h light- and 8 h light cycle at 25° C. (day) and 23° (night), at a relative humidity of 70%. Barley plants were grown with a 16 h light- and 8 h dark-rhythm at 18° C. and 65% relative humidity. After incubation with *Magnaporthe oryzae*, barley plants were kept for 24 h at 24-26° C. and 100% relative humidity before being covered with a plastic hood and cultivated under the growing conditions described above.

All references cited herein are incorporated by reference with respect to their entire disclosure content.

The following Examples shall illustrate the invention. They shall, however, not be construed as limiting the scope of the invention.

Example 1: Methods

Experimental Model and Subject Details
*Arabidopsis Arabidopsis thaliana* plants were grown individually in pots containing a mixture of soil (Substrat BP3; Klasmann-Deilmann), vermiculite, and sand (8:1:1) in an enviromentally controlled cultivation chamber with a 10-h-day (9 AM to 7 PM)/14-h-night cycle. Relative humidity in the growth chambers was adjusted to 60% and day and night temperatures were set to 21° C. and 18° C., respectively. For inoculation experiments with *Pseudomonas syringae* (metabolite and isotope-labeling studies, assessment of basal resistance), 5- to 6-week-old plants with an unstressed, uniform appearance were used, whereas experiments with *Hyaloperonospora arabidopsidis* were performed with 3- to 4-week-old, naïve plants, if not stated otherwise. The ald1 and fmo1 mutants represent the SALK lines SALK_007673 and SALK_026163, respectively (Mishina and Zeier, 2006; Návarová et al., 2012). Further sid2-1 (sid2, ics1), npr1-2 (npr1, NASC ID: N3801), pad4-1 (pad4), sard4-5 (sard4; GABI_428E01) and eds1-2 (eds1) were used in this study (see Bernsdorff et al., 2016 and Hartmann et al., 2017 for a more detailed description). All *Arabidopsis* mutant lines used are in the Col-0 background.

*Pseudomonas*
*Pseudomonas syringae* pv maculicola ES4326 (Psm) and Psm carrying the *Photorhabdus luminescens* luxCDABE operon (Psm lux) were grown at 28° C. in King's B medium containing the appropriate antibiotics (concentrations: rifampicin 50 µg L-1, kanamycin 50 µg L-1, tetracycline 15 µg L-1) under permanent shaking (Hartmann et al., 2017; Fan et al., 2008). For experiments, overnight log-phase cultures were washed four times with 10 mM MgCl$_2$ solution and diluted to different final OD$_{600}$ levels for leaf inoculation as detailed in the respective sections. In general, the diluted bacterial solutions as well as mixtures thereof containing metabolites of interest, such as labelled isotopes, were carefully pressure infiltrated from the abaxial side of the leaves using a needleless syringe.

*Hyaloperonospora arabidopsidis* (Downy Mildew)

The oomycete *Hyaloperonospora arabidopsidis* (Hpa) is the causal agent of downey mildew in the model plant *Arabidopsis* and has been extensively studied in the context of host/pathogen co-evolution (Slusarenko and Schlaich, 2003). Due to its obligate biotrophic lifecycle, Hpa has to be maintained on a weekly basis on susceptible *Arabidopsis* accessions and mutants to ensure its survival. In our study, *Arabidopsis* Col-0 wildtype plants were used for the propagation of the compatible Hpa isolate Noco2 (Bartsch et al., 2006; kind gift from Professor Jane Parker, MPIPZ Cologne). Therefore, 2 weeks old *Arabidopsis* plants (50-100 individuals/pot) were spray-inoculated with a conidio-spore suspension (5×10$^4$ conidiospores per mL of water) until the leaves were saturated. The inoculated plants were then maintained on sealed trays with a transparent lid under short day (10 hours light period/18° C. during day and night) and high humidity conditions (>90% humidity) in an environmentally controlled growth chamber (Percival Scientific: Model SE-41).

Method Details
GC-MS Analysis of Metabolites

In this study, two major analytical procedures for plant metabolite extraction and derivatization were used. The first method converts free carboxylic acids into their respective methyl esters after sample derivatization with trimethylsilyl-diazomethane. This optimizes GC separation of organic acids (Schmelz et al., 2004; Hartmann et al., 2017). This procedure was mainly used for the initial identification of NHP from plant tissues and analysis of enzyme assays. The second method is based on the trimethylsilylation of carboxyl-, hydroxyl- and amino-groups of the sample analytes and was employed for the quantification of NHP and other target metabolites in plant tissue and as an alternative procedure of identification for NHP.

The first method has been described in detail previously (Návarová et al., 2012; Hartmann et al., 2017). Levels of NHP and other metabolites in *Arabidopsis* leaf samples or from enzyme activity assays were determined after solvent extraction of the samples material followed by a vapour-phase extraction-based work up of the extracts and subsequent analysis of the resulting derivatized samples. Shock-frozen leaf material (approximately 100-200 mg pooled from up to six leaves) was ground to a fine powder using a pre-chilled ball mill and immediately homogenized with 600 µl of extraction buffer, consisting of $H_2O$:1-propanol:HCl (1:2:0.005). In the case of enzyme assays, 50-100 µl of the aqueous assays were used and extracted as described above. After the addition of 100 ng of $D_4$-salicylic acid as internal standard, 1 ml of methylene chloride was added and the mixture was thoroughly re-homogenized (>30 sec) and then centrifuged at 14000×g for 1 min to achieve optimal phase separation. For the analyses of NHP, the lower organic phase was removed, dried with $Na_2SO_4$, and incubated with 4 µl of 2 M trimethylsilyl-diazomethane in hexane (Sigma-Aldrich) for 5 min at room temperature, driving the conversion of carboxylic acids into the corresponding methyl esters. The methylation reaction was stopped by addition of an excess of acetic acid (4 µl of a 2 M solution in hexane) to the vials, and the sample was then subjected to a vapour phase extraction procedure at 70° C. and 200° C. under a steady stream of nitrogen by using a volatile collector trap packed with Porapak-Q absorbent (Porapak-Q absorbent (VCT-1/4X3-POR-Q; Analytical Research Systems) according to Schmelz et al. (2004). The volatilized and trapped metabolites were then eluted from the absorbent with 1 ml methylene chloride. Finally, the sample volume was reduced to 30 µl in a stream of nitrogen prior to GC-MS analysis. 4 µl of the resulting sample mixture were then separated on a gas chromatograph (GC 7890A; Agilent Technologies) equipped with a fused silica capillary column (ZB5 MS, Zebron) and mass spectra were recorded with a 5975C mass spectrometric detector (Agilent Technologies) in the electron ionization (EI) mode as described before (Návarová et al., 2012; Hartmann et al., 2017). NHP was analyzed by the selected ion chromatogram of mass-to-charge ratio (m/z) 100.

For the second method, 40-60 mg of freshly pulverized, frozen leaf tissue were extracted twice with 1 ml of MeOH/$H_2O$ (80:20, v/v) extraction buffer. The buffer for the initial extraction step was additionally supplemented with various internal standards, including $d_9$-Pip (1000 ng) for the quantification of Pip, $D_4$-SA (500 ng) for the quantification of SA and 2-hydroxy-cyclohexanecarboxylic acid (2-HCC; 1000 ng) for the quantification of NHP. During each individual extraction step, samples were first homogenized thoroughly by vortexing (>30 sec), then incubated on a rotary mixer (150 rpm/min) at 4° C. for at least 5 min. Afterwards samples were centrifuged for 2 min at 14000×g and the supernatants from both extraction steps (2 ml total volume) combined into one 2 ml Eppendorf vial. At this stage, samples could be stored for several days at −80° C. For subsequent derivatization, aliquots of 400 to 800 µl of this extract were evaporated to dryness using a ScanSpeed vacuum centrifuge (Labogene ApS, Denmark). The derivatization procedure itself started with the addition of 20 µl pyridine, followed by 20 µl N-Methyl-N-trimethylsilylfluoroacetamide (MSTFA) containing 1% TCMS (v/v) and 60 µl of hexane. Between each pipetting step, the sample vials were thoroughly vortexed. The resulting reaction mixture was first incubated for 30 min at 70° C. and then allowed to cool down at room temperature for an additional 30 min. Finally, aliquots of the samples were transferred to a GC vial and diluted 5 to 10-fold with hexane. 2 µl of the sample mixture were then separated on a gas chromatograph (GC 7890A; Agilent Technologies) equipped with a fused silica capillary column (Phenomenex ZB-35; 30 m×0.25 mm×0.25 µm) and mass spectra were recorded with a 5975C mass spectrometric detector (Agilent Technologies) in the electron ionization (EI) mode. The GC oven temperature program was as follows: initial temperature of 70° C. for 2 min, followed by a gradient to 320° C. at a rate of 10° C./min, followed by a final hold time of 5 min (Total run time: 32 min). For quantitative determination of individual metabolites, peaks originating from selected chromatograms of a specific m/z ration were integrated and quantified by relating the areas of a substance peak to the peak area of the corresponding internal standard (IS): NHP (m/z 172)/IS: 2-HCC (m/z 273); Pip (m/z 156)/IS: $D_9$-Pip (m/z 165); SA (m/z 267)/IS: D4-SA (m/z 271). Correction factors experimentally determined for each substance by use of authentic substances were considered. Metabolite levels were related to leaf fresh weight.

GC-FTIR Analysis of Metabolites

GC-IRD spectra were acquired as detailed in Hartmann et al. (2017). Briefly, spectra were recorded with a resolution of 16 $cm^{-1}$ and a scan rate of eight scans per second using a Hewlett-Packard 6890 Series gas chromatograph coupled with an IRD3 infrared detector manufactured by ASAP analytical (Analytical Solutions and Providers, Covington, KY—USA). The IRD method parameters were as follows: Resolution=16; Apodization=Triangle; Phase correction=Mertz; Zero-Fill=1; Co-Add=2. Flow cell and the transfer line temperatures were both set to 250° C. Nitrogen was used as sweep gas. The GC was operated in splitless mode using helium as carrier gas, with a flow rate adjusted to 2 mL/min and a column head pressure of 9.54 psi. The GC-IRD studies were carried out with a fused silica capillary column (Zebron ZB-5; 30 m×0.32 mm×0.25 µm) purchased from Phenomenex Corporation (Aschaffenburg, Germany). The GC oven temperature program was as follows: an initial temperature of 50° C. for 3 min, ramped up to 240° C. for 8 min, followed by a ramping step to 320° C. over the course of 20 min (Total time: 33.75 min). In general, 1-4 µl of a respective, derivatized sample were injected using an Agilent 7863 Series autoinjector. To simplify the identification of relevant target peaks, all method parameters including the derivatization of the samples by diazomethane (yielding methylesters of carboxylic acids), the GC column, as well as the temperature program used in our GC-IRD studies were identical to those used in the complementing GC-MS studies.

Chemical Synthesis of N-Hydroxypipecolic Acid (NHP)

Authentic 1-hydroxypiperidine-2-carboxylic acid (N-hydroxypipecolic acid) was synthesized according to a protocol of Murahashi and Shiota (1987). 0.232 g of $Na_2WO_4$ (0.70 mmol) were dissolved in 12 ml of water. To this solution, an amount of 1.5 g of piperidine (17.62 mmol) was added and the solution cooled down to 0° C. An aqueous 30% solution of $H_2O_2$ in water was added slowly (4.02 ml, 39.55 mmol $H_2O_2$). The resulting solution was stirred for further 3 h at 0° C. Then, 1.72 g of potassium cyanide (26.41 mmol) was added to the solution, followed by the careful addition of 6.3 ml 4 N aqueous HCl. The reaction mixture was stirred for 4 h at 0-10° C. Afterwards, the solution was adjusted to pH 9 with 2 N of aqueous KOH solution. The product was extracted with dichloromethane and the solvent was evaporated under reduced pressure. 1.47 g of 1-hydroxypiperidine-2-carbonitrile (11.65 mmol, 66%) were isolated. 1 g (7.93 mmol) of this product was dissolved in 13 ml concentrated HCl an heated until reflux for 18 h. Removal of the solvent under reduced pressure yielded 1.76 g (7.49 mmol, 94%) 1-hydroxypiperidine-2-carboxylic acid hydrochloride with nearly equimolar amounts of ammonium chloride.

$^1$H-NMR (300 MHz, DMSO-$d_6$): δ=11.90 (brs, COOH), 7.43 (t, $^1J_{NH}$=50.8 Hz, NH$_4$), 4.08 (dd, $^3J_{HH}$=11.9, 3.3 Hz, 1H, CH), 3.66-3.57 (m, 1H), 3.27 (ddd, $^3J_{HH}$=11.5, 11.4, 4.6 Hz, 1H), 2.20-2.08 (m, 1H), 1.88-1.61 (m, 5H), 1.57-1.41 (m, 1H) ppm. $^{13}$C-{$^1$H}-NMR (75 MHz, DMSO-$d_6$): δ=168.8 (s, COOH), 68.4 (s, NCCOOH), 57.2 (s), 39.5 (s), 27.2 (s), 22.5 (s), 20.36 (s) ppm. MS (EI): m/z (%)=146 ([M]$^+$, 5), 128 ([M-OH]$^+$, 5), 100 ([M-COOH]$^+$, 80). Anal. Calcd. for $C_6H_{16}Cl_2N_2O_3$ (235.10, equimolar ratio of amino acid hydrochloride and NH$_4$Cl): C 30.65, H 6.86, N 11.92. Found C 31.60, H 6.72, N 11.66.

Plant Treatments with Pip and NHP

Treatments with Pip and NHP were essentially performed as detailed for Pip in Návarová et al. (2012). NHP was synthesized according to the protocol published by Murahashi and Shiota (1987). With respect to P. syringae resistance assays, 10 ml of a 1 mM aqueous solution of Pip or NHP (equates to 10 μmol) were pipetted onto the soil of individually cultivated 5-week-old plants. The same exogenous application of 10 ml H$_2$O served as a control treatment. With respect to Hpa resistance assays, 3 to 4-week olds plants were cultivated in batches of four plants per pot and treated as described above. Inoculation with P. syringae or Hpa was performed 24 h after the plant pre-treatment as described below.

Assessment of Plant Resistance to P. syringae

To assess bacterial growth in naive 5-week-old plants, overnight log phase cultures of Psm lux were washed three times with 10 mM MgCl$_2$ and diluted to a final optical density at 600 nm (OD$_{600}$)=0.001 before infiltrating the resulting bacterial suspensions from the abaxial side into three fully grown leaves of either untreated or pre-treated Arabidopsis plants (compare section: Plant treatments with Pip and NHP) using a 1-mL syringe without a needle. The infiltration was performed between 10 and 11 AM. Approximately 60 hours later, the bacterial growth was quantified by measuring the bacterial bioluminescence in leaf discs (10 mm in diameter) of infiltrated leaves (one disc per leaf, three discs per plant) using a Serius FB12 luminometer (Berthold Detection Systems). Bacterial growth rates were displayed as relative light units per cm$^2$ of leaf area (Fan et al., 2008). For each independent experiment, at least 20 replicate leaves from six to seven plants per treatment and plant genotype were measured before performing a statistical analysis of the resulting values. All pathogen experiments depicted in the figures were repeated several times with similar results.

Assessment of Plant Resistance to Hpa 3 to 4-week old plants were spray-inoculated with a suspension of conidiospores (5*10$^4$ ml$^{-1}$) of the Hpa isolate Noco2 as described before. 7 days after inoculation, leaves of plants were photographed to document the presence/absence of disease symptoms and then harvested and stained with Trypan-blue for further microscopic analysis.

Trypan Blue Staining

Trypan blue staining was performed loosely based on the protocol described by Koch and Slusarenko (1990) to enable the identification and quantitative analysis of disease stages and resistance phenotypes (Uknes et al., 1992; Slusarenko and Schlaich, 2003; Bartsch et al., 2006). Briefly, leaves of Hpa-inoculated plants were harvested in 50 ml conical tubes (Falcon) and covered with trypan blue solution, more specifically lactic acid-phenol-trypan blue solution, consisting of 1 mg/ml trypan blue, 25% [w/v] lactic acid, 25% water-saturated phenol [v/v], and 25% glycerol [v/v] in water. The fully submerged samples were incubated overnight at 37° C. under permanent shaking (200 rpm). The trypan blue solution was replaced the next day by a 2.5 g/ml chloral hydrate aqueous solution and incubated under the same conditions until the leaves were decolorized. Finally, the chloral hydrate was replaced with 50% glycerol for further storage or mounting of the samples on microscope slides prior to their examination under a light microscope equipped with interference or phase-contrast optics.

Microscopic analysis of Hpa infection Microscopic photographs of Trypan blue-stained leaves were acquired with a Zeiss Axiocam 105 color camera coupled to a bright field microscope (Zeiss AxioStar Plus, Carl Zeiss Ltd.) operated by Zeiss ZenCore software. In addition, leaf overview images were captured with a Canon EOS 6D DSLR camera equipped with a Canon MP-E 65 mm Macro f/2.8 manual focus lens and a light table adjusted to daylight conditions (5500 Kelvin) as light source. Leaf images were subsequently analyzed using the ImageJ-based analysis software bundle Fiji (Schindelin et al., 2012). Leaf surface areas, the lengths of free intercellular hyphae (IH; FIG. 5B, image I), and the lengths of intercellular hyphae encased by trailing necrotic cells (TN; FIG. 5B, image IV) were determined in overview shots with the freehand line selection tool and the measuring function of Fiji. Beforehand, the length scale was set in Fiji using photographs of a calibrated benchmark taken under the same photographic and microscope settings as the leaf images. Total IH were calculated as the sum of free IH and IH encased in TN. The number of oospores (OS; FIG. 5B, image III) were determined in leaf photographs with the multi point tool of Fiji. The number of conidiophores (CP; FIG. 5B, image II) on the leaf samples was assessed by direct microscopic examination of sample slides and counting of CPs with the help of marked 1 mm-grids. In order to minimize the variation of measurements, the parallel leaf samples were examined and photographed with the same microscope settings. To reduce user-generated bias, the images were additionally randomized and analyzed independently.

Treatment with Isotope-Labelled Metabolites

In planta labelling experiments were performed by infiltrating three to four mature leaves of 5-week-old soil-grown Arabidopsis wild-type Col-0 and relevant mutant plants in the morning with Psm (OD$_{600}$=0.005) or MgCl$_2$ (mock controls) as described before (Section: Assessment of Plant Resistance to P. syringae). Four hours after the initial inoculation, the same leaves were infiltrated with 5 mM solutions of the isotope-labelled L-Lys varieties L-Lys-6-$^{13}$C-ε-$^{15}$N (CAS 204451-46-7; Sigma-Aldrich) and L-Lys-4,4,5,5-d$_4$ (d$_4$-Lys) (Cambridge Isotope Laboratories) prepared in HPLC-grade water. DL-2-piperidine-d$_9$ carboxylic acid (D$_9$-Pip; Aldrich 688444) was co-infiltrated at a final concentration of 1 mM as part of the final bacterial suspension. In all cases, water infiltrations served as control treatments. Infiltrated leaves were harvested at 48 hpi (counting from the first infiltration event with Psm or mock treatment) and subsequently extracted, derivatized, and analyzed by GC-MS according to the described protocols.

Cloning of FMO1 cDNA fragments corresponding to FMO1 (At1g19250) were PCR-amplified using high-fidelity Phusion polymerase (New England Biolabs) as recommended by the manufacturer. The gene sequence of FMO1 (NCBI Reference Sequence accession number: NM_101783.4) was introduced into the target vector pET32b(+) (Novagen) using sticky-end cloning (Zeng, 1998) between restriction sites NdeI and XhoI. The resulting recombinant protein thus contained eight non-native residues at the C terminus, including the polyHistidine tag. Primer sequences can be found in the Key resources table. Plasmids harbouring the respective genes were transformed into chemically competent *E. coli* BL21 Rosetta™ 2(DE3) pLysS cells (Novagen) and plated on LB-Agar plates containing the appropriate selection markers. Positive transformants carrying the gene of interest were identified by colony PCR using the same gene-specific primers used for the initial amplification and were verified by sequencing.

Purification of Recombinant FMO1 Enzyme

A single colony of recombinant *E. coli* BL21 Rosetta™ 2(DE3) pLysS cells containing FMO1 inserted into pET32b vector was picked and cultured overnight in 3 ml of lysogeny broth (LB) medium supplemented with the appropriate selection markers at 37° C. and with constant shaking on an orbital shaker before inoculating and growing a 500-1000 ml culture under the same conditions until the $OD_{600}$ reached 0.5-0.8. At this point the culture was briefly cooled down and the transgene expression was induced with 0.5 mM isopropyl-β-D-1-thiogalactopyranoside (IPTG), followed by incubation overnight at 16°-25° C. with constant shaking (240 rpm). Generally, the best results were obtained with freshly transformed cells and incubation at reduced temperatures (16° C.) after induction of transgene expression to minimize the precipitation of recombinant enzymes as insoluble inclusion bodies. Satisfying results were also obtained with shorter incubation times (5 h at 28° C. after induction with IPTG), even though it should be mentioned that we initially also met severe solubility problems as reported for other N-hydroxylating flavoprotein monooxygenases in the past (summarized by Olucha and Lamb, 2011). The bacterial pellets were collected by centrifugation at 6000×g for 15 min at 4° C. (Eppendorf R5810). The pellet was then re-suspended in a minimum of extraction/binding buffer (50 mM sodium phosphate, pH 8.0, 500 mM NaCl, 10% glycerol, 20 mM imidazole, 5 mM β-mercaptoethanol, 1 mM PMSF). For bigger culture volumes (>500 ml), the resulting homogenate was transferred to a pre-cooled mortar and ground in liquid nitrogen with a pestle until a homogenous white powder was obtained. The powder was then transferred to 2 ml Eppendorf tubes and allowed to thaw on ice. The resulting homogenate was then precipitated using a centrifuge at 20000×g for 30 min at 4° C. The cell-free supernatants containing soluble recombinant protein were collected, pooled and filtered through a low-protein binding nylon filter (0.22 μm) before being applied to a pre-equilibrated immobilized immune affinity chromatography (IMAC) column, such as a nickel-charged His GraviTrap™ affinity column (GE Healthcare, Germany) or cobalt-charged HisTALON™ Gravity column (Takara Bio, USA) (1 ml). After the initial binding step, the column was successively washed according to the respective manufacturers recommendations. The proteins were then eluted with 50 mM sodium phosphate buffer, pH 8.0, containing up to 500 mM NaCl and 200 mM imidazole and collected in fractions of 0.75 ml. Using those conditions, most of the enzyme activity was found to be in 4-5 consecutive fractions, which were combined and desalted using a 5-mL desalting PD10 column (GE Healthcare) equilibrated with a low-salt buffer, containing 100 mM potassium phosphate buffer (pH 8), containing 10% (v/v) glycerol and 1 mM DTT. Aliquots of the purified proteins were used for the quantification of total protein content by the Bradford method using the Bradford Assay reagent (Bio-Rad, Dusseldorf, Germany) according to the manufacturer's protocol. Bovine serum albumin (Albumine fraction V) was used for the standard curve. Target enzyme purity was determined by SDS-polyacrylamide gel electrophoresis on a 12% gel according to Laemmli's method (results not shown). Due to the relative instability of the purified recombinant protein (loss of 90% of its activity within 24 h of the purification), the majority of the enzymes was used directly for activity assays and the remaining protein was flash frozen in liquid nitrogen and stored at −80° C. in 20% Glycerol for later analysis.

FMO1 Activity Assays

FMO1 enzyme assays were designed based on the knowledge about mechanistic and structural studies of the few characterized N-hydroxylating flavoprotein monooxygenases (Olucha and Lamb, 2011). In general, standard assays were carried out with 50 mM sodium phosphate buffer, pH 8.0, containing 50 μg $g^{-1}$ recombinant FMO1 protein, 400 μM NADH, 10 mM L-pipecolic acid, and 200 μM flavin adenine dinucleotide ($FAD^+$) at 30° C. All reaction mixtures contained 5% glycerol for additional enzyme stability and were incubated for up to 16 h. Reactions were stopped by inactivating the enzyme at 85° C. for 10 min. The formation of NHP was monitored using GC-MS after derivatization of the assays with the methylating reagent trimethylsilyl-diazomethane as described above. Reactions without enzyme or heat-inactivated FMO1 enzyme were systematically performed as controls. All assays were repeated at least in triplicates.

Example 2: Results

FLAVIN-DEPENDENT MONOOXYGENASE1 Functions as a Pipecolic Acid N-Hydroxylase

FMO1 is an indispensable component of SAR and required for the hitherto described Pip-inducible immune responses in *Arabidopsis*, i.e. the establishment of resistance to bacterial pathogens (Návarová et al., 2012), the activation of defense priming (Bernsdorff et al., 2016), and the induction of immune-related gene expression. Because of this central downstream function of FMO1 in Pip signal transduction, and since several flavin-dependent monooxygenases from animals, fungi, and bacteria are involved in the N-oxidation of nitrogen-containing substrates (Rossner et al., 2017), we previously hypothesized that FMO1 might metabolize Pip to an N-oxidized derivative required for immune activation (Zeier, 2013). We therefore aimed at elucidating the biochemical function of the FMO1 monooxygenase, both by in planta and in vitro strategies.

On one hand, we performed comparative gas chromatography-mass spectrometry (GCMS)-based metabolite analyses of leaf extracts from Psm-inoculated and mock-control plants of wild-type Col-0, ald1 mutants, and fmo1 mutants. We first applied sample derivatization with trimethylsilyl-diazomethane to convert analytes with free carboxylic acid groups into methyl esters which facilitates their GC-MS analyses (Schmelz et al., 2004; Hartmann et al., 2017). When analyzing GC-MS ion chromatograms of mass-to-charge ratio (m/z) 100, we identified a specific substance peak (Ta) in the leaf samples of the Psm-treated wild-type plants that was absent in any of the mock-control samples, and in samples of Psm-treated ald1 and fmo1 (Figure TA). The mass spectrum of substance 1a exhibited a dominant m/z 100 ion (a possible N-hydroxypiperidine fragment) and a putative M⁺ ion of m/z 159, which corresponds the mass of methylated (derivatized) N-hydroxypipecolic acid (FIG. 1C). We further applied gas chromatography-Fourier transform infrared spectroscopy (GC-FTIR) to obtain an infrared (IR) spectrum of compound 1a (FIG. 1D). This IR spectrum showed close similarity to a spectrum in the IR database, N-methyl-pipecolic acid methylester, but possessed an additional band at 3595 cm$^{-1}$ that is characteristic for O—H stretching vibrations (FIG. 1D;). This corroborated the assumption that substance 1a possibly represented derivatized N-hydroxypipecolic acid. We therefore chemically synthesized N-hydroxypipecolic acid (1-hydroxypiperidine-2-carboxylic acid) according to a protocol of Murahashi and Shiota (1987) (see Method details). GC-MS analysis of derivatized samples showed that the mass spectra and retention times of the synthetically generated N-hydroxypipecolic acid (NHP) and the identified plant-derived substance were identical, demonstrating that *Arabidopsis* produces NHP in an ALD1- and FMO1-dependent manner in response to Psm inoculation.

As a next step, we overexpressed C-terminally polyhistidine-tagged FMO1 enzyme in *Escherichia coli* and purified the protein via immobilized metal ion affinity chromatography and a subsequent desalting step to adjust buffer conditions for activity assays. L-Pip was then tested in vitro as a substrate of recombinant FMO1 enzyme in the presence of the presumed co-factors flavin adenine dinucleotide (FAD⁺) and NADH. After incubation of the assays overnight at 30° C., FMO1 assays were stopped and derivatized with trimethylsilyl-diazomethane to produce methyl esters of substrates and reaction products and analyzed via GC-MS. In the presence of FAD⁺ and NADH as cofactors, purified FMO1 protein was able to catalyze the conversion of L-Pip to NHP in in vitro assays, whereas none of the controls lacking either the substrate, the purified FMO1 enzyme or one of the co-factors led to the N-hydroxylation of L-Pip to produce NHP (FIG. 1B)

For quantitative determination of NHP in plant tissue, we developed a second GC-MS-based method that employs trimethylsilylation of hydroxyl- and amino-groups of the sample analytes through N-Methyl-N-trimethylsilylfluoroacetamide (MSTFA). With this procedure, NHP is silylated both at the N—OH and the carboxyl OH group. The mass spectrum of the derivatized NHP (1b) shows a dominant ion of m/z 172, a small but discernable M⁺ ion at m/z 289, and a M⁺—CH₃ fragment ion at m/z 274 (FIG. 1H). By use of the single ion chromatogram of m/z 172, NHP could be robustly quantified in plant extracts (FIG. 2), and comparative extract analyses confirmed that NHP is only biosynthesized in Psm-inoculated Col-0 but not in ald1 or fmo1 plants (FIG. 1E). To further define the biosynthetic pathway of NHP in *Arabidopsis*, we fed plants with isotope-labelled D$_9$-Pip and concomitantly inoculated them with Psm. In addition to unlabeled NHP, we observed the in planta generation of D$_9$-labelled NHP (FIGS. 1F, 1I). Similarly, when 4,4,5,5-D$_4$-Lys was co-applied with Psm to plants, we observed, in addition to D$_4$-labelled Pip (Hartmann et al., 2017), the co-occurrence of the corresponding D$_4$-labelled NHP in the extracts (1G and 1H). Isotope-labelled D$_9$-NHP (from D$_9$-Pip feeding) and D$_4$-NHP (from D$_4$-Lys feeding) were also detected with the alternative GC-MS procedure that uses analyte derivatization by methylation (not shown). In addition, when feeding the Lys isotopic variant L-Lys-6-$^{13}$C,ε-$^{15}$N to Psm-inoculated Col-0, the in planta generation of $^{13}$C,$^{15}$N-labelled NHP was observed (not shown). Together, these in planta and the above-described in vitro studies indicate that *Arabidopsis* produces NHP in response to pathogen inoculation by the FMO1-catalysed N-hydroxylation of L-Pip (FIG. 1), which itself is biosynthesized via an ALD1-mediated α-transamination of L-Lys (Hartmann et al., 2017).

N-Hydroxypipecolic Acid Accumulates Systemically in the *Arabidopsis* Foliage at the Onset of Biologically-Induced SAR A hallmark of the plant defensive metabolism associated with SAR constitutes the pathogen-induced accumulation of the immune regulators SA and Pip in 1°-inoculated and in distal, 2° leaves (Bernsdorff et al., 2016). To characterize the endogenous generation of NHP in *Arabidopsis* in response to pathogen attack, we determined the levels of NHP in 1° and 2° leaves of Col-0 plants at different times after Psm-inoculation and mock-treatment. Over the whole time course, NHP was not detected in the mock-treated control plants (FIG. 2A). In Psm-inoculated leaves, however, NHP was produced from 10 hpi onwards, with the onset of local NHP generation timely coinciding with the rise of Pip (FIG. 2A). At 24 hpi, the NHP levels reached a maximum of about 30 µg g$^{-1}$ FW, which was quantitatively similar to the amount of Pip that had accumulated at this stage of infection (FIG. 2A). At 48 hpi, the levels of NHP decreased to about half of the maximum value (16 µg g$^{-1}$ FW) in the attacked leaves whereas Pip further accumulated to more than 100 µg g$^{-1}$ FW, revealing a divergence in the accumulation patterns of NHP and Pip at this later stage of infection. The SAR response in the distal, 2° leaves of Col-0 plants inoculated in 1° leaves with Psm starts to develop not earlier than 24 hpi and is established at 48 hpi under the applied experimental conditions (Mishina et al., 2007; Návarová et al., 2012; Bernsdorff et al., 2016). Moreover, in our previous experiments, the systemic levels of Pip and SA did not begin to increase before 30 hpi (Návarová et al., 2012). In accordance with the previous findings, both Pip and SA significantly accumulated in the 2° leaves at 48 hpi but not yet at 24 hpi in the present time course analyses. By contrast, albeit to quantitatively modest levels in the range of 0.15 µg g$^{-1}$ FW, a significant and reproducible accumulation of NHP was detected already at 24 hpi in the 2° leaves of 1°-leaf-inoculated plants (FIG. 2A). Subsequently, the systemic levels of NHP reached a maximum of about 1.5 to 2 µg g$^{-1}$ FW at 48 hpi and then declined to levels of 0.5 µg g$^{-1}$ FW at 72 hpi (FIG. 2A). Together, these time course analyses show that NHP is biosynthesized to high amounts in the 1°-inoculated leaves in response to Psm attack and also substantially accumulates in the distant, 2° leaves. Moreover, the systemic NHP accumulation starts comparatively early at the very onset of SAR induction.

NHP Generation in *Arabidopsis* Completely Depends on the Biosynthetic Genes ALD1 and FMO1 and is Tightly Regulated by the Immune Regulators EDS1 and PAD4

We next examined the Psm-induced generation of NHP and Pip in different *Arabidopsis* mutants with defects in key immune regulatory genes in inoculated leaves at 24 and 48 hpi (FIG. 2B). As indicated before (FIG. 2; Návarová et al., 2012), the accumulation of both NHP and Pip was absent in the ald1 mutant (FIGS. 2B and 2C), which is defective in the ALD1-catalysed transamination of L-Lys and the subsequent formation the Pip precursor 2,3-DP (Hartmann et al., 2017). The reductase SARD4 largely contributes to the reduction of 2,3-dehydropipecolic acid to Pip, and, as previously reported (Ding et al., 2016; Hartmann et al., 2017), we found that a sard4 knockout mutant (sard4-5) biosynthesizes markedly lower levels of Pip upon Psm inoculation than the wild-type (FIG. 2B). Similarly, with 0.3 and 1.9 µg g$^{-1}$ FW at 24 and 48 hpi, respectively, the sard4-5 mutant only generated a small fraction of the NHP that accumulated in wild-type plants (FIG. 2B). Moreover, fmo1 strongly generated Pip at the sites of Psm inoculation (Návarová et al., 2012), but was completely defective in NHP biosynthesis (FIG. 2B), suggesting that FMO1 constitutes the single pipecolic acid N-hydroxylase in *Arabidopsis*. Together with the in vitro and isotope-labelling studies (FIG. 1; Hartmann et al., 2017), the phenotypes of the ald1, sard4, and fmo1 mutants show that NHP is synthesized upon pathogen-inoculation by a reaction sequence that involves three enzymatic steps: α-transamination of L-Lys by the aminotransferase ALD1, subsequent reduction of the intermediate 2,3-DP to Pip by SARD4 (and other reductive activities), and finally N-hydroxylation of Pip by FMO1 (FIG. 3).

The two interacting partners EDS1 and PAD4 constitute key control units of *Arabidopsis* basal immunity and are required for the proper expression of distinct defense genes as well as for strong activation of SA biosynthesis upon pathogen recognition (Zhou et al., 1998; Feys et al., 2001; Rietz et al., 2011). Functional PAD4 proved also necessary for effective induction of ALD1 and FMO1 expression, and for Pip biosynthesis. In addition, EDS1 positively regulates FMO1 expression (Song et al., 2004a; Bartsch et al., 2006; Mishina and Zeier, 2006; Návarová et al., 2012). Together, this suggests a role for the EDS1/PAD4 signaling node in regulating the induction of NHP biosynthesis. To directly test this, we examined Pip and NHP levels in Psm-inoculated eds1 and pad4 mutant plants. With levels of 3.8 and 4.6 $\mu g\ g^{-1}$ FW in inoculated eds1 and pad4 leaves, respectively, Pip only accumulated to about 14 and 17% of the wild-type levels in these mutants at 24 hpi (FIG. 2B). Furthermore, NHP accumulated to amounts of 0.4 and 0.7 $\mu g\ g^{-1}$ FW at 24 h post Psm inoculation in the eds1 and pad4 leaves, which accounted for only 1.3 and 2.4% of the wild-type levels, respectively (FIG. 2C). With about 0.15 $\mu g\ g^{-1}$ FW for both eds1 and pad4, the NHP levels were even lower at 48 hpi. These data illustrate that the biosynthesis of NHP is tightly controlled by the EDS1/PAD4 immune regulatory node, evidently at both the levels of Pip generation and Pip hydroxylation. We next asked for a possible regulatory function of the SA pathway in NHP production and examined the Psm-triggered NHP accumulation in the SA-deficient mutant sid2 and in the SA-insensitive mutant npr1. Surprisingly, the two mutant lines accumulated significantly higher levels of NHP than the wild-type in Psm-inoculated leaves at both 24 and 48 hpi (FIG. 2C). For example, with 119 and 56 $\mu g\ g^{-1}$ FW for sid2 and npr1, respectively, NHP levels were about four- and two-fold higher at 24 hpi than in the wild-type (FIG. 2C), and the levels in sid2 further rose to 260 $\mu g\ g^{-1}$ FW at 48 hpi. Therefore, NHP accumulation does not require a functional SA signaling pathway, and SA even appears to prevent the accumulation of NHP to very high levels. Pip did neither over-accumulate in sid2 nor in npr1, indicating that the negative regulatory effect of SA on the accumulation of surplus NHP operates downstream of Pip biosynthesis (FIG. 3).

Exogenous NHP Acts as a Potent Inducer of Plant Immunity to Bacterial and Oomycete Infection and Abolishes the Resistance Defects of Fmo1

Together, the biochemical function of FMO1 as an NHP-generating pipecolic acid N-hydroxylase, the concurrent key role of the flavin monooxygenase in SAR and Pip-mediated immune responses, and the substantial systemic accumulation of NHP in the SAR-induced wild-type suggested a critical role for NHP in plant acquired resistance to pathogen infection. To verify this hypothesis, we tested whether exogenously applied NHP would, in a similar manner than Pip, induce resistance of wild-type plants to *P. syringae* infection, and unlike Pip, override the acquired resistance defect of the NHP-deficient fmo1 mutant. To this end, we supplied individual plants with doses of 10 μmol Pip (10 ml of a 1 mM aqueous solution), 10 μmol NHP or 10 ml water as a control treatment, leaf-inoculated plants 1 d later with *P. syringae*, assessed bacterial growth at 60 hpi, and documented the disease symptoms of the inoculated plants at 72 hpi (FIG. 3). To assess bacterial growth, we used a bioluminescent Psm strain that expresses the *Photorhabdus luminescens* luxCDABE operon (Psm lux) which allows quantification of bacterial in leaves in a non-destructive manner via luminescence measurements (Fan et al., 2008; Hartmann et al., 2017).

The inoculated leaves of the non-pre-treated Col-0, ald1, and fmo1 control plants exhibited pronounced chlorotic disease symptoms after three days (FIG. 3A), and this was accompanied with high bacterial numbers in leaves. The leaves of ald1 and fmo1 mutants hosted significantly higher amounts of bacteria than the leaves of the Col-0 wild-type at 60 hpi (FIG. 3B), confirming that basal resistance to Psm is attenuated in these mutants (Návarová et al., 2012). Consistent with previous results, the pre-treatment of plants with Pip strongly increased disease resistance of wild-type and ald1 plants (Návarová et al., 2012; Bernsdorff et al., 2016), as illustrated by the suppression of the development of chlorotic leaf symptoms in inoculated Col-0 and ald1 leaves and ten-fold lower bacterial multiplication in the leaves of Pip-treated compared with the leaves of control plants (FIGS. 3A and 3B). By contrast, fmo1 plants remained susceptible after the Pip-treatment, since inoculated leaves of Pip-treated fmo1 plants developed strong tissue chlorosis and allowed high bacterial multiplication to levels similar to those of non-pre-treated fmo1 (FIGS. 3A and 3B).

This confirms that exogenous Pip is able to override the defect in acquired resistance of the Pip biosynthetic mutant ald1 but not of the fmo1 mutant (Návarová et al., 2012; Bernsdorff et al., 2016).

Significantly, pre-treatment of plants with NHP strongly increased resistance to bacterial infection in Col-0, ald1, and fmo1, which manifested itself by a lack of the chlorotic symptom development and by the attenuation of Psm lux growth by at least one order of magnitude in all the genotypes (FIGS. 3A and 3B). Therefore, NHP functions as a potent inducer of acquired resistance to *P. syringae* infection in *Arabidopsis*. Importantly, and in contrast to exogenous Pip, exogenous NHP also complements the acquired resistance defect of the NHP biosynthesis mutant fmo1. These resistance phenotypes and the biochemical function of FMO1 as a pipecolate N-hydroxylase demonstrate that the FMO1-mediated conversion of Pip to NHP in response to pathogen inoculation and the subsequent accumulation of NHP are critical for the acquired resistance response in *Arabidopsis* (FIGS. 1 to 4). Moreover, the previously described resistance effects of Pip are attributable to the accumulation of NHP which is generated from Pip by FMO1.

Pathogen-induced SAR in *Arabidopsis* depends on a major, SA-dependent and a minor, SA-independent signaling mode which both require an intact Pip biosynthetic pathway and FMO1 (Bernsdorff et al., 2016). To analyze the significance of SA signaling for the NHP-mediated immune response, we compared the effects of exogenous NHP on resistance to Psm lux in the SA biosynthesis-defective sid2 mutant and in the Col-0 wild-type. The sid2 mutant is substantially compromised in basal resistance to *P. syringae* infection (Nawrath and Métraux, 1999), and this manifested itself by several-fold higher bacterial numbers in the leaves of non-pretreated sid2 plants compared to Col-0 plants at 60 h post Psm lux inoculation (FIG. 3C). The bacterial numbers in the leaves of NHP-pretreated sid2 were about 2.5-fold lower at 60 hpi than those of naive sid2 plants, indicating that NHP induced a significant resistance response in the SA-deficient mutant (FIG. 3C). However, this resistance effect was markedly lower in sid2 than in Col-0, since a ten-fold difference in bacterial numbers between control and NHP-treated plants was determined for the wild-type (FIG. 3C). Exogenous application of the NHP precursor Pip evoked similar resistance responses in sid2 (and in Col-0) than exogenous NHP (FIG. 3C). Together, these data indicate that the full potential of NHP in mediating plant acquired resistance is only realized in association with an intact SA signaling pathway, although an SA-independent component of NHP-inducible immunity also exists. The acquired resistance effects obtained by direct NHP application and by biological SAR induction therefore follow comparable mechanistic principles (Bernsdorff et al., 2016).

Since SAR confers broad spectrum resistance of plants against hemibiotrophic and biotrophic pathogens (Sticher et al., 1997), we examined whether acquired resistance induced by NHP or Pip application would also protect *Arabidopsis* against a second pathogen of this class, the biotrophic oomycete *Hyaloperonospora arabidopsidis* (Hpa). After the inoculation of leaves with oomycete spores and spore germination, virulent Hpa strains invade *Arabidopsis* leaves by direct penetration at the junction of two epidermal cells and intercellular growth of hyphae in the leaf interior that is accompanied with the budding of haustoria into leaf cells. Asexual reproduction of the downy mildew pathogen involves the outgrowth of conidiospore-bearing conidiophores through stomates which develop a macroscopically visible, white lawn on the leaf surface. Concomitantly, sexual oospores form in globular oogonia outside the leaf (Slusarenko and Schlaich, 2003).

Figure 5C:
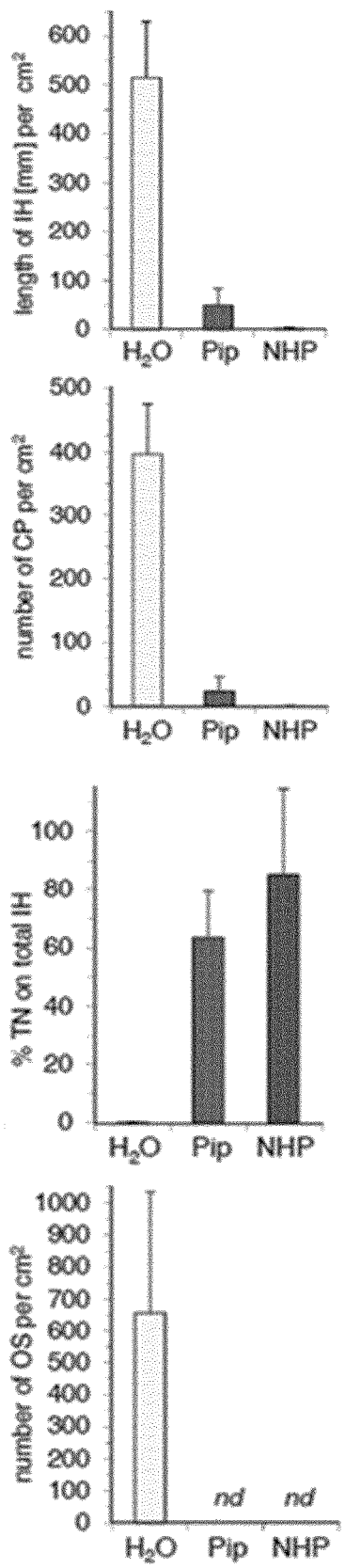
Figure 5D:
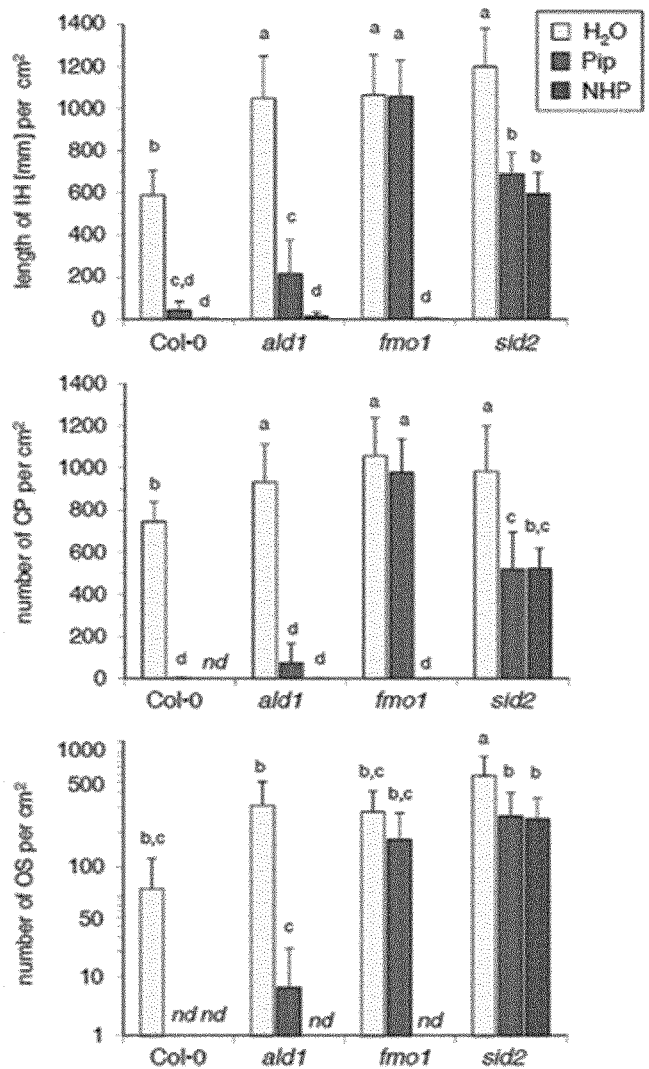

Seven days after leaf-inoculation of untreated four or five week-old Col-0 plants with the virulent Hpa isolate Noco2 (Bartsch et al., 2006), we observed extensive areas of whitish downy mildew symptoms on the inoculated leaves (FIG. 5A). At the microscopic level, leaves were pervaded with intercellular hyphae (IH) which we visualized by Trypan blue staining (FIG. 5B, image I, FIG. 6). A quantitative assessment determined average lengths of about 500 mm per cm$^2$ leaf area for the intercellular hyphae at 7 dpi (FIG. 5C). Moreover, conidiophores (CPs) densely developed on the leaf surfaces (FIG. 5B, image II; FIG. 5C), and the majority of leaf samples were covered with several hundreds of oospores (OS) per cm$^2$ leaf area (FIG. 5B, image III; FIG. 5C). The macroscopically visible mildew symptoms were generally more pronounced on the leaf surfaces of untreated ald1, fmo1, and sid2 plants than on the leaves of wild-type Col-0 plants (FIG. 5A), and the quantitative microscopic assessments revealed the presence of more extended intercellular hyphae, as well as higher numbers of conidiophores and oospores in association with the leaves of the three mutants compared with those of Col-0 (FIG. 5D). This indicates that basal resistance of *Arabidopsis* to Hpa is dependent on functional ALD1, FMO1, and SID2, and therefore on intact Pip/NHP and SA signaling.

In contrast to control plants, the Pip-pretreated Col-0 plants were largely symptom-free at the macroscopic level and only occasionally contained small areas of visible mildew symptoms (FIG. 5A). Moreover, the average length of intercellular hyphae growing inside leaves was reduced to about 50 mm cm$^{-2}$ (~10% of the value for non-pretreated Col-0 plants) (FIG. 5C). Unlike naive plants, about 60% of the intercellular hyphae in leaves of the Pip-treated plants were closely encased by dead host cells (FIG. 5B, image IV, FIG. 6), a plant defense reaction to Hpa previously designated as trailing necrosis (Uknes et al., 1992). In addition, Pip-pretreatment greatly diminished the occurrence of conidiophores on leaves and fully prevented the development of oospores at 7 dpi (FIG. 5C, FIG. 6). Thus, the pretreatment of Col-0 plants with Pip strongly reduced their susceptibility to Hpa infection. The same protective effect of exogenous Pip was also observed for ald1, although the level of resistance to Hpa seemed somewhat smaller for Pip-treated ald1 than for Pip-treated Col-0 plants (FIGS. 5A, 5D). Therefore, exogenous Pip is able to largely restore acquired resistance to Hpa in the Pip-deficient ald1 mutant. By contrast, Pip pre-treatment had no effect on the resistance of fmo1 to Hpa (FIG. 5A, 5D), indicating that, as for *P. syringae* infection, the fmo1 defect in acquired resistance to Hpa is not complemented by exogenous Pip.

Remarkably, Col-0 plants pre-treated with 10 μmol NHP before Hpa inoculation were completely free of mildew symptoms at 7 dpi (FIGS. 5A, 5D). Moreover, Trypan blue-stained leaves of inoculated, NHP-supplemented plants generally resembled stained leaves of non-inoculated plants (FIG. 6), except that sporadically, microscopic lesions consisting of one or a few dead cells were discernable. These were reminiscent of a highly localized hypersensitive response (HR) (FIG. 5B, image V). In addition, the invasive growth of Hpa inside the leaves of NHP-pretreated plants was effectively blocked. About 70% of the examined leaves fully prohibited the formation of intercellular hyphae at 7 dpi (FIG. 5C), while for the remaining 30%, a very rare and limited occurrence of short hyphae inside leaves (length between 0.5 to 2 mm cm$^2$) was observed. These rudimentary hyphae were usually accompanied with a trailing necrotic reaction of the plant (FIG. 5C). Further, the NHP-pretreatment completely inhibited the development of conidiophores and oospores on Col-0 leaves after Hpa inoculation (FIG. 5C). Therefore, the application of a micromole dose of NHP to wild-type Col-0 offers effective plant protection against Hpa infection, and this protection is even more complete than the resistance effect evoked by the same dose of Pip (FIGS. 5 and 6).

This strong NHP-triggered resistance to Hpa was not only induced in the Col-0 wild-type, but also in ald1 and, most importantly, in fmo1 (FIGS. 5A, 5D). Thus, exogenous NHP restores the acquired resistance defect of the NHP-deficient fmo1 mutant towards infection by both the bacterial pathogen Psm and the oomycete Hpa. Moreover, although NHP and Pip feeding also provoked a discernable reduction of the mildew symptoms, intercellular hyphal growth, conidiophore formation and oospore development in Hpa-inoculated sid2, application of the substances were finally not able to fully prevent disease development in the SA-deficient mutant (FIGS. 5A, 5D).

Taken together, our findings indicate that the here-described pathogen-inducible L-Lys catabolic pathway that includes the ALD1-dependent biosynthesis of Pip and its subsequent FMO1-mediated conversion to NHP possesses a central functional role in the *Arabidopsis* acquired resistance response. This acquired resistance program is switched on as a consequence of accumulating NHP in plants and, in addition, requires the pathogen-inducible biosynthesis of SA to exploit its full protective potential against pathogen invasion (FIG. 3).

NHP Biosynthetic Pathway Metabolites in the Course of Host-Pathogen-Interactions Accumulate in Various Plant Species (See Also FIG. 8)

As shown in FIG. 8, Pip and NHP could be detected various monocotelydonous and dicotelydonous plant species after inoculation with compatible pathogens. The results are summarized in Table 1 below. The table summarizes the results on the resistance effects after NHP pretreatment.

as in some primary aliphatic diamines such as putrescine (Olucha and Lamb, 2011). For example, Orn hydroxylase from *Pseudomonas aeruginosa* catalyzes the formation of $N^5$-hydroxy-ornithine which is subsequently formylated and incorporated into the iron-chelating siderophore pyoverdin (Meneely et al., 2009).

The biosynthesis of NHP in *Arabidopsis* proceeds by the FMO1-mediated N-hydroxylation of the secondary amino

TABLE 1

Overview - NHP accumulation in selected monocotyledonous and dicotyledonous plants after inoculation with compatible pathogens and resistance effects after NHP pre-treatment

| Model plant (Plant family) | Monocot/Dicot | Pathogen used | Type | life cycle |
|---|---|---|---|---|
| *Arabidopsis thaliana* (Brassicacae) | Dicot | *Pseudomonas syringae* | bacterial | hemibiotrophic |
| | | *Hyaloperonospora arabidopsidis* | oomycete | hemibiotrophic |
| *Solanum lycopersicum* (Solanaceae) | | *Pseudomonas syringae* pv. tomato DC3000 | bacterial | hemibiotrophic |
| | | *Phytophthora infestans* | oomycete | hemibiotrophic |
| *Nicotiana tabacum* cv. Xanthi (Solanaceae) | | *Pseudomonas syringae* pv. tabaci (DSM 1856) | bacterial | hemibiotrophic |
| *Glycine max* (Fabaceae) | | *Pseudomonas syringae* subsp. *savastanoi* (DSM 50267) | bacterial | hemibiotrophic |
| *Hordeum vulgare* (Poaceae) | Monocot | *Magnaporthe oryzae* | ascomycete | biotrophic |
| *Zea mays* (Poaceae) | | *Ustilago maydis* | basidiomycetous fungus | biotrophic |

| Model plant (Plant family) | NHP biosynthetic pathway metabolites accumulation in response to pathogen | | | Resistance effect after NHP pre-treatment |
|---|---|---|---|---|
| | time point (dpi) | Pip | NHP | |
| *Arabidopsis thaliana* (Brassicacae) | 2 | ++++ | ++++ | Yes |
| | 7 | ++ | + | Yes |
| *Solanum lycopersicum* (Solanaceae) | 2 | +++ | ++ | not tested yet |
| | 5 | +++ | ++ | not tested yet |
| *Nicotiana tabacum* cv. Xanthi (Solanaceae) | 2 | +++ | +++ | Yes |
| *Glycine max* (Fabaceae) | 9 | ++ | ++ | not tested yet |
| *Hordeum vulgare* (Poaceae) | 5 | ++++ | + | not tested yet |
| *Zea mays* (Poaceae) | 3 | ++ | + | not tested yet |

(Table legend: dpi = days past infection; accumulation: ++++ very strong, +++ strong, ++ moderate, +detectable*)

DISCUSSION

In the current study, we have identified the previously undescribed, N-hydroxylated amino acid N-hydroxypipecolic acid as a novel, endogenously produced *Arabidopsis* metabolite with a critical role in plant acquired resistance to pathogen infection (FIG. 3). NHP was not detected in unstressed, naïve plants but strongly accumulated in *P. syringae*-challenged leaves to levels of about 30 μg $g^{-1}$ FW (FIG. 2). Until now, N-hydroxylated substances have rarely been described as plant-derived natural products. While oximes that contain a hydroxylated $sp^2$-hybridized nitrogen are well-characterized intermediates in the biosynthesis of glucosinolates and cyanogenic glucosides (Sibbesen et al., 1995; Wittstock and Halkier, 2000), hydroxylated, $sp^3$-nitrogen-containing amines or amino acids such as NHP have, to our knowledge, not been reported before as natural plant constituents. However, bacteria and fungi use N-hydroxylating monooxygenases to hydroxylate the primary amino groups in the side chains of L-Lys and L-Orn, as well group in the piperidine ring of Pip (FIGS. 1 and 3). *Arabidopsis* FMO1 thus catalyzes a biochemical N-hydroxylation reaction similar to those of bacterial N-hydroxylating monooxygenases. The substrates and the biochemistry for the characterized plant FMOs from clade II and III are different from those of the clade I-associated FMO1. While the so far characterized clade III FMOs are involved in the S-oxygenation of sulfides to sulfoxides within the biosyntheses of sulfur-containing plant secondary metabolites (Li et al., 2008; Yoshimoto et al., 2015), the clade II YUCCAs mediate the oxidative decarboxylation of indole-3-pyruvate to the plant hormone IAA (Mashiguchi et al., 2011), a reaction which does not require a direct oxygenation of a heteroatom. All hitherto characterized plant FMOs, however, have endogenous substrates and catalyse biochemical reaction within defined metabolic pathways. These characteristics apparently contrast those of human FMOs, which are known to mediate the oxidative degradation of a broad range of heteroatom-containing xenobiotics (Cashman and Zhang, 2006).

L-Lys catabolism in plants comprises the sacchopine pathway that generates the dicarboxylic, non-protein amino acid α-amino adipic acid and the lysine decarboxylase-catalyzed biosynthesis of the diamine cadaverine (Galili et al., 2001; Bunsupa et al., 2012; Zeier, 2013). Our work has now identified a novel pathogen-inducible L-Lys catabolic pathway in plants that culminates in the accumulation of NHP (FIGS. 1 2 and 3). The activation of this pathway already starts at the level of the precursor amino acid Lys, whose leaf levels rise in response to pathogen attack (Návarová et al., 2012). In a first enzymatic step, the alpha-$NH_2$-group of L-Lys is transferred to an acceptor oxoacid, preferentially pyruvate, in an aminotransferase reaction catalyzed by ALD1 (FIG. 3; Hartmann et al., 2017; Ding et al., 2016). The resulting, in planta detectable Lys catabolic product is 2,3-dehydropipecolic acid (2,3-DP), which accumulates to moderate levels in locally inoculated and systemic leaves of Arabidopsis (Hartmann et al., 2017). 2,3-DP can be formed from the initial Lys transamination product, the α-ketoacid KAC, by dehydrative cyclization and subsequent keto-enol tautomerization of the intermediate 1,2-dehydropipecolic acid (FIG. 3). Although recombinant ALD1 protein is able to accept several amino acids other than L-Lys as in vitro substrates (Song et al., 2004b), combined in vitro studies and in planta analyses indicate that the α-transamination of L-Lys to 2,3-DP is the predominant in vivo function of ALD1 (Hartmann et al., 2017).

In a second enzymatic step, the NAD(P)H-dependent reductase SARD4, a plant orthologue of the mammalian reductase CRYM (Hallen et al., 2011; Hartmann et al., 2017), and a yet to identify further reductive activity reduce dehydropipecolic acid intermediates to Pip (FIG. 3). Pip accumulates after P. syringae attack to high levels in locally inoculated and systemic leaves of Arabidopsis plants (Návarová et al., 2012; FIG. 3B), and has been identified as a pathogen- and stress-inducible amino acid in many other plant species (e.g. Pálfi and Dézsi, 1968; Vogel-Adghough et al., 2013; Aliferis et al., 2014; Masclaux-Daubresse et al., 2014). Subcellular localization studies with transgenic plants expressing ALD1- and SARD4-reporter proteins suggest that Pip, like the precursor amino acid L-Lys, is synthesized in plastids (Sharma et al., 2013; Cecchini et al., 2015).

We demonstrated here by both in vitro and in planta analyses that the final enzymatic step in the biosynthesis of NHP is the FMO1-catralyzed, NAD(P)H- and $O_2$-dependent N-hydroxylation of Pip to NHP (FIGS. 1, 2 and 3). The biosynthetic scheme from L-Lys to NHP depicted in FIG. 3 is fully supported by our plant feeding experiments with L-Lys-4,4,5,5-$d_4$, L-Lys-6-$^{13}$C,ε-$^{15}$N, and $D_9$-Pip, because the isotope-labelled NHP variants synthesized in planta in the course of a leaf inoculation show the biosynthetic derivation of NHP from L-Lys and Pip, and the involvement of the ALD1-mediated L-Lys α-transamination step in both Pip and NHP biosynthesis (FIG. 2; Hartmann et al., 2017).

The inducible character of the NHP biosynthetic pathway is reflected by the findings that the expression of ALD1, SARD4, and FMO1 is strongly enhanced in response to pathogen attack, both in the locally inoculated and in the systemic leaves (Song et al., 2004a; Mishina and Zeier, 2006; Bernsdorff et al., 2016; Hartmann et al., 2017). Interestingly, all the NHP biosynthetic genes are also up-regulated by elevated Pip, indicating that the accumulating precursor Pip amplifies NHP biosynthesis by both feedback and feedforward stimulation at the transcriptional level (FIG. 3). In addition, NHP generation is tightly regulated by the interacting defense signaling partners PAD4 and EDS1 (Feys et al., 2001), since pad4 and eds1 mutants only accumulated about 0.5 to 2% of the NHP amounts of wild-type plants in response to P. syringae (FIG. 2C). Consistently, previous studies revealed that up-regulation of the NHP biosynthetic genes ALD1 and FMO1 is positively stimulated by the EDS1/PAD4 regulatory node (FIG. 3; Song et al., 2004a; Bartsch et al., 2006; Mishina and Zeier, 2006; Návarová et al., 2012). Furthermore, it is likely that the transcriptional control of NHP biosynthesis also involves the two transcription factors SARD1 and CBPG60, because chromatin immunoprecipitation analyses suggested that they target the promoters of several plant defensive genes including those of ALD1 and FMO1 (Sun et al., 2015).

The establishment of SAR is dependent on or positively influenced by a set of signal-active metabolites and regulatory proteins (reviewed in Shah and Zeier, 2013). Since the initial discoveries of ALD1 and FMO1 as important SAR players (Song et al., 2004a; Mishina and Zeier, 2006), numerous studies from different laboratories have confirmed the indispensability of these genes for SAR induction under variable conditions (e.g. Jung et al., 2009; Liu et al., 2011; Chaturvedi et al., 2012; Návarová et al., 2012), including an unbiased mutant screen for SAR-related genes (Jing et al., 2011). These findings indicate that the Pip/NHP biosynthetic pathway constitutes a core and indispensable element of SAR. Significantly, all of the hitherto known responses to Pip, i.e. systemic resistance induction, establishment of defense priming, and direct induction of SAR gene expression, are dependent on functional FMO1 (FIG. 1A; Návarová et al., 2012; Gruner et al., 2013; Bernsdorff et al., 2016). The defense phenotypes of fmo1 and the now elucidated biochemical function of FMO1 as NHP-generating pipecolate hydroxlase indicate that NHP is the actual mediator of the immune responses previously assigned to Pip (Návarová et al., 2012). This is verified by our finding that exogenous NHP—but not Pip—fully restores the capacity to acquire resistance towards P. syringae and Hpa attack in the NHP-deficient fmo1 mutant (FIGS. 4, 5. and 6). Together, this indicates that NHP constitutes a critical metabolic regulator of SAR in Arabidopsis.

SAR equips plants with broad-spectrum immunity to a range of different biotrophic and hemibiotrophic phytopathogens (Sticher et al., 1997). Accordingly, we have established that NHP effectively mediates acquired resistance to pathogen types with distinct phylogenetic origin and inherently different mode of infection, i.e. the hemibiotrophic bacterium P. syringae and the biotrophic oomycete Hpa (Katagiri et al., 2002; Slusarenko and Schlaich, 2003). A 10 μmol dose of exogenously applied NHP enhances resistance of Arabidopsis to P. syringae with at least the same efficiency than the same dose of Pip (FIG. 4), and it is reasonable to assume that the above-mentioned direct induction of defense-related gene expression and the establishment of a primed state significantly contribute to these protective effects.

Strikingly, the NHP pre-treatment converted the compatible Hpa-Arabidopsis interrelation that is associated with massive invasive growth of intercellular hyphae and the development of numerous epiphytically-situated reproductive oomycete structures virtually into a symptomless, incompatible interaction (FIGS. 5 and 6). In most of the leaves of the NHP-pretreated plants, the invasive growth of the oomycete was fully prohibited, and reproductive structures were totally absent. These leaves essentially resembled leaves of non-inoculated plants, as evident at the macroscopic level and microscopically in Trypan blue-stained leaves (FIG. 6). The occurrence of scattered, microscopic HR lesions in the leaves of NHP-pretreated and Hpa-inoculated plants suggests that highly localized hypersensitive cell death events, possibly at sites of attempted oomycete penetration, might contribute to this strong, NHP-mediated resistance effect (FIG. 5B, image V, FIG. 6). In the very rare cases when short intercellular hyphae had developed in the leaves of NHP-pretreated plants, they were usually surrounded by necrotic plant cells, suggesting that a trailing necrosis reaction had effectively stopped the extension of hyphae very early after oomycete entry into leaves (FIG. 5C). The observed protective effect of the natural immune regulator NHP towards Hpa infection is reminiscent of the previously described action of the synthetic resistance enhancer 2,6-dichloroisonicotinic acid (INA) (Uknes et al., 1992). Consistent with the here-identified function of FMO1 as NHP synthase, overexpression of FMO1 in transgenic Arabidopsis resulted in comparable protection to Hpa invasion and P. syringae attack than NHP-pretreatment (Koch et al., 2006; Bartsch et al., 2006). Moreover, Bartsch and colleagues have generated Arabidopsis lines overexpressing FMO1 variants that code for proteins in which conserved Gly residues in either the FAD- or NADPH-binding motifs of FMO1 were changed to Ala. Expression of these protein variants in plants did not confer enhanced protection, indicating and corroborating our present finding that the enzymatic activity of FMO1 is required for its role in immunity (Bartsch et al., 2006).

Exogenous Pip also conferred significant resistance to wild-type plants against Hpa infection, but not to the same absolute level as NHP treatment (FIG. 5B). In Pip-pretreated plants, intercellular hyphae were more frequent than in NHP-fed plants, although most of them were encased by trailing necrotic cells, and, sporadically, conidiophores developed on leaves. The necessity for the plant to still convert Pip into NHP for resistance activation after Pip-treatment, which is circumvented by direct NHP application, might account for this difference.

Our time-course analyses indicate that the systemic increase of NHP in the distal leaves of P. syringae-inoculated plants starts at the very onset of the SAR response at 24 hpi, already before systemic Pip and SA accumulation is observable (FIG. 2A). These early systemic rises in NHP might be caused by the translocation from 1°-inoculated leaves, in which the compound accumulates to high levels (FIG. 2), to the distant 2° leaves. Alternatively, rapid systemic signaling processes might induce early expression of FMO1 in the 2° leaves, and FMO1 in turn catalyzes the hydroxylation of Pip which is present to low basal levels also in non-induced plants. For example, reactive oxygen species (ROS) have been implicated in rapid systemic defense signal transduction and SAR (Alvarez et al., 1998; Dubiella et al., 2013; Wang et al., 2014), and ROS-generating treatments proved sufficient to trigger FMO1 expression in Arabidopsis leaves (Olszak et al., 2006). In view of the early systemic increase of NHP at the onset of SAR and its strong resistance-inducing potential, future studies on the function of NHP in systemic defense signaling transduction might further improve our mechanistic understanding of SAR.

Previous genetic analyses in Arabidopsis indicated that ALD1 and/or FMO1 mediate plant resistance by partially SA-independent signaling modes (Song et al., 2004a; Bartsch et al., 2006; Zhang et al., 2008). Moreover, our recent study suggested that a Pip/FMO1 regulatory module mediates SAR by both SA-independent and SA-dependent activation pathways (Bernsdorff et al., 2016). Consistently, Pip/FMO1-derived NHP triggered a significant acquired resistance response in the SA-deficient sid2 mutant. However, NHP clearly required inducible SA biosynthesis to provide strong protection against P. syringae or Hpa invasion, suggesting a synergistic interplay of NHP and SA in resistance induction (FIGS. 4C, 5A, and 5D). At the level of NHP biosynthesis, by contrast, a negative regulatory action of SA on NHP generation was evident, particularly at later infection stages (Figure). A comparable negative effect of SA on the accumulation of Pip was not observed (FIG. 2B). This suggests that increased SA levels attenuate the pathogen-induced accumulation of NHP to excess levels at the stage of Pip to NHP conversion (FIG. 3). In line with this assumption, we observed a stronger pathogen-inducible expression of FMO1 in the SA-deficient sid2 mutant than in the SA-accumulating wild-type (Bernsdorff et al., 2016). The molecular structures of NHP and SA resemble each other, particularly with respect to the presence of similarly arranged carboxylic acid and hydroxyl functional groups. Whether this structural resemblance determines the biological function of and the interplay between NHP and SA in plant immunity remains to be determined.

In conclusion, our studies have identified a novel pathogen-inducible L-Lys catabolic pathway in Arabidopsis that generates N-hydroxypipecolic acid, a previously undescribed plant metabolite with a central function in plant acquired resistance to pathogen infection. We show that the final enzymatic step in NHP biosynthesis constitutes the FMO1-catalyzed N-hydroxylation of Pip. Since the NHP precursor Pip is widely distributed in angiosperms and FMO1 orthologues exist in other plant species, we consider it likely that L-Lys catabolism to NHP constitutes a common plant metabolic pathway. Consistently, recent analyses show that NHP accumulates in tomato inoculated with the oomycete Phytophtora infestans or the bacterium Pseudomonas syringae, in tobacco inoculated with Pseudomonas tabaci, in soybean inoculated with Pseudomonas savanastoi, in barley inoculated with the ascomycetous fungus Magnaporthe oryzae, and in maize inoculated with the basidiomycetous fungus Ustilago maydis (FIG. 8A-D; Table 1). This shows that the NHP biosynthetic pathway exists in both monocotyledonous and dicotyledonous plants. Moreover, exogenous application of low doses of NHP confers effective protection to Arabidopsis against attack by pathogen types with inherently different modes of infection. In addition, leaf infection of tobacco in response to Pseudomonas tabaci inoculation was prevented by the pre-treatment of plants with a dose of 40 µmol NHP (FIG. 8D). Since Arabidopsis and tobacco are not closely related species, it can be expected that the exogenous treatment with NHP induces plant disease resistance in a broad spectrum of other angiosperm plants. Our method therefore promises general applicability for inducing plant disease resistance to pathogens and to contribute to the development of novel, natural product-based plant protection strategies.

REFERENCES

Aliferis, K. A., Faubert, D., and Jabaji, S. (2014). A metabolic profiling strategy for the dissection of plant defense against fungal pathogens. PLoS One 9: e111930.

Alonso, J. M., et al. (2003). Genome-wide insertional mutagenesis of Arabidopsis thaliana. Science 301: 653-657.

Alvarez, M. E., Pennell, R. I., Meijer, P.-J., Ishikawa, A., Dixon, R. A., and Lamb, C. (1998). Reactive oxygen intermediates mediate a systemic signal network in the establishment of plant immunity. Cell 92, 773-784.

Attaran, E., Zeier, T. E., Griebel, T., and Zeier, J. (2009). Methyl salicylate production and jasmonate signaling are not essential for systemic acquired resistance in *Arabidopsis*. Plant Cell 21: 954-971.

Bartsch, M., Gobbato, E., Bednarek, P., Debey, S., Schultze, J. L., Bautor, J., and Parker, J. E. (2006). Salicylic acid-independent ENHANCED DISEASE SUSCEPTIBILITY1 signaling in *Arabidopsis* immunity and cell death is regulated by the monoxygenase FMO1 and the nudix hydrolase NUDT7. Plant Cell 18: 1038-1051.

Benjamini, Y., and Hochberg, Y. (1995). Controlling the false discovery rate: a practical and powerful approach to multiple testing. J Roy Statist Soc Ser B (Methodological) 57: 289-300.

Bernsdorff, F., Döring, A.-C., Gruner, K., Schuck, S., Bräutigam, A., and Zeier, J. (2016). Pipecolic acid orchestrates plant systemic acquired resistance and defense priming via salicylic acid-dependent and -independent pathways. Plant Cell 28: 102-129

Brady, S. M., Burow, M., Busch, W., Carlborg, Ö., Denby, K. J., Glazebrook, J., Hamilton, E. S., Harmer, S. L., Haswell, E. S., Maloof, J. N., Springer, N. M., and Kliebenstein, D. J. (2015). Reassess the t Test: Interact with All Your Data via ANOVA. Plant Cell 27: 2088-2094.

Bräutigam, A., Kajala, K., Wullenweber, J., Sommer, M., Gagneul, D., Weber, K. L., Carr, K. M., Gowik, U., Mass, J., Lercher, M. J., Westhoff, P., Hibberd, J. M., and Weber, A. P. (2011). An mRNA blueprint for C4 photosynthesis derived from comparative transcriptomics of closely related C3 and C4 species. Plant Physiol 155: 142-156.

Bunsupa, S., Katayama, K., Ikeura, E., Oikawa, A., Toyooka, K., Saito, K., and Yamazaki, M. (2012). Lysine decarboxylase catalyzes the first step of quinolizidine alkaloid biosynthesis and coevolved with alkaloid production in Leguminosae. Plant Cell 24, 1202-1216.

Burow, M., and Halkier, B. A. (2017). How does a plant orchestrate defense in time and space? Using glucosinolates in *Arabidopsis* as case study. Curr. Opin. Plant Biol., 38, 142-147.

Cashman, J. R., and Zhang, J. (2006). Human flavin-containing monooxygenases. Annu. Rev. Pharmacol. Toxicol. 46, 65-100.

Cecchini, N. M., Jung, H. W., Engle, N. L., Tschaplinski, T. J., and Greenberg, J. T. (2015) ALD1 regulates basal immune components and early inducible defense responses in *Arabidopsis*. Mol. Plant Microbe Interact. 28, 455-466.

Chaturvedi, R., Venables, B., Petros, R. A., Nalam, V., Li, M., Wang, X., Takemoto L. J., and Shah, J. (2012). An abietane diterpenoid is a potent activator of systemic acquired resistance. Plant J. 71, 161-172.

Cheng, Y., Zhou, Y., Yang, Y., Chi, Y. J., Zhou, J., Chen, J. Y., Wang, F., Fan, B., Shi, K., Zhou, Y. H., Yu, J. Q., and Chen, Z. (2012). Structural and functional analysis of VQ motif-containing proteins in *Arabidopsis* as interacting proteins of WRKY transcription factors. Plant Physiol 159: 810-825.

Chen, W., Li, X., Tian, L., Wu, P., Li, M., Jiang, H., Chen, Y., and Wu, G. (2014). Knockdown of LjALD1, AGD2-like defense response protein 1, influences plant growth and nodulation in *Lotus japonicus*. J. Integr. Plant Biol. 56, 1034-1041.

Cui, H., Tsuda, K., and Parker J. E. (2015). Effector-triggered immunity: from pathogen perception to robust defense. Annu. Rev. Plant Biol. 66, 487-511.

Charles et al. Neurochemical Research, Vol. 11, No. 4, 1986, pp. 521-525

Camañes, G., Scalschi, L., Vicedo, B., González-Bosch, C., and García-Agustin, P. (2015). Plant J 84, 125-139.

Dai, X., Mashiguchi, K., Chen, Q., Kasahara, H., Kamiya, Y., Ojha, S., DuBois, J., Ballou, D., and Zhao, Y. (2013). The biochemical mechanism of auxin biosynthesis by an *Arabidopsis* YUCCA flavin-containing monooxygenase. J. Biol. Chem. 288, 1448-1457.

Delaney, T. P., Friedrich, L., and Ryals, J. A. (1995). *Arabidopsis* signal transduction mutant defective in chemically and biologically induced disease resistance. Proc Natl Acad Sci USA 91: 8955-8959.

Ding, P., Rekhter, D., Ding, Y., Feussner, K., Busta, L., Haroth, S., Xu, S., Li, X., Jetter, R., Feussner, I., and Zhang, Y. (2016). Characterization of a pipecolic acid biosynthesis pathway required for systemic acquired resistance. Plant Cell 28, 2603-2615.

Dubiella, U., Seybold, H., Durian, G., Komander, E., Lassig, R., Witte, C. P., Schulze, W. X., and Romeis, T. (2013). Calcium-dependent protein kinase/NADPH oxidase activation circuit is required for rapid defense signal propagation. Proc Natl Acad Sci USA 110: 8744-8749.

Fan, J., Crooks, C., and Lamb, C. (2008). High-throughput quantitative luminescence assay of the growth in planta of *Pseudomonas syringae* chromosomally tagged with *Photorhabdus luminescens* luxCDABE. Plant J. 53, 393-399.

Feys, B. J., Moisan, L. J., Newman, M. A., and Parker, J. E. (2001). Direct interaction between the *Arabidopsis* disease resistance signaling proteins, EDS1 and PAD4. EMBO J. 20: 5400-5411.

Fu, Z. Q., and Dong, X. (2013). Systemic acquired resistance: turning local infection into global defense. Annu Rev Plant Biol. 64: 839-863.

Galili, G., Tang, G., Zhu, X., and Gakiere, B. (2001) Lysine catabolism: a stress and development super-regulated metabolic pathway. Curr. Opin. Plant Biol. 4, 261-266.

Garcia-Seco, D., Chiapello, M., Bracale, M., Pesce, C., Bagnaresi, P., Dubois, E., Moulin, L., Vannini, C., and Koebnik, R. (2017). Transcriptome and proteome analysis reveal new insight into proximal and distal responses of wheat to foliar infection by *Xanthomonas translucens*. Sci Rep 7, 10157.

Garcion, C., Baltensperger, R., Fournier, T., Pasquier, J., Schnetzer, M. A., Gabriel, J. P., and Métraux, J.-P. (2006). FiRe and microarrays: a fast answer to burning questions. Trends Plant Sci 11: 320-322.

Goda, H. et al. (2008). The AtGenExpress hormone and chemical treatment data set: experimental design, data evaluation, model data analysis and data access. Plant J 55: 526-542.

Gruner, K., Griebel, T., Návarová, H., Attaran, E., and Zeier, J. (2013). Reprogramming of plants during systemic acquired resistance. Front Plant Sci 4: 252.

Hallen, A., Cooper, A. J., Jamie, J. F., Haynes, P. A., and Willows, R. D. (2011). Mammalian fore-brain ketimine reductase identified as µ-crystallin; potential regulation by thyroid hormones. J. Neurochem. 118, 379-387.

Hartmann, M., Kim, D., Bernsdorff, F., Ajami-Rashidi, Z., Scholten, N., Schreiber, S., Zeier, T., Schuck, S., Reichel-Deland, V., and Zeier, J. (2017). Biochemical principles and functional aspects of pipecolic acid biosynthesis in plant immunity. Plant Physiol. 174, 124-153.

Hartmann, M., Zeier, T., Bernsdorff, F., Reichel-Deland, V., Kim, D., Hohmann, M., Scholten, N., Schuck, S., Bräutigam, A., Hölzel, T., Ganter, C., and Zeier, J. (2018).

Flavin monooxygenase-generated N-hydroxypipecolic acid is a critical element of plant systemic immunity. Cell 173, 456-469.

Huijbers, M. M., Montersino, S., Westphal, A. H., Tischler, D., and van Berkel, W. J. (2014). Flavin dependent monooxygenases. Arch. Biochem. Biophys. 544, 2-17.

Jing, B., Xu, S., Xu, M., Li, Y., Li, S., Ding, J., and Zhang, Y. (2011). Brush and spray: a high-throughput systemic acquired resistance assay suitable for large-scale genetic screening. Plant Physiol 157: 973-980.

Jirage, D., Tootle, T. L., Reuber, T. L., Frost, L. N., Feys, B. J., Parker J. E., Ausubel, F. M., and Glazebrook, J. (1999). *Arabidopsis thaliana* PAD4 encodes a lipase-like gene that is important for salicylic acid signaling. Proc Natl Acad Sci USA 96: 13583-13588.

Jung, H. W., Tschaplinski, T. J., Wang, L., Glazebrook, J., and Greenberg, J. T. (2009). Priming in systemic plant immunity. Science 324: 89-91.

Jung, G. Y., Park, J. Y., Choi, H. J., Yoo, S.-J., Park, J.-K., and Jung, H. W. (2016). A Rice Gene Homologous to *Arabidopsis* AGD2-LIKE DEFENSE1 Participates in Disease Resistance Response against Infection with *Magnaporthe oryzae*. Plant Pathol. J. 32, 357-362.

Katagiri, F., Thilmony, R., and He, S. Y. (2002). The *Arabidopsis thaliana-Pseudomonas syringae* interaction. *Arabidopsis* Book 1, e0039.

Kiyota, E., Pena, I. A., and Arruda, P. (2015). The saccharopine pathway in seed development and stress response of maize. Plant Cell Environ. 38, 2450-2461.

Koch, E., and Slusarenko, A. (1990). *Arabidopsis* is susceptible to infection by a downy mildew fungus. Plant Cell 2, 437-445.

Koch, M., Vorwerk, S., Masur, C., Sharifi-Sirchi, G., Olivieri, N., and Schlaich, N. L. (2006). A role for a flavin-containing monooxygenase in resistance against microbial pathogens in *Arabidopsis*. Plant J 47: 629-639.

Lawrence, J. M., and Grant, D. R. (1963). Nitrogen Mobilization in Pea Seedlings. II. Free Amino Acids. Plant Physiol 38, 561-566.

Li, J., Hansen, B. G., Ober, J. A., Kliebenstein, D. J., and Halkier, B. A. (2008) Subclade of flavin-monooxygenases involved in aliphatic glucosinolate biosynthesis. Plant Physiol. 148, 1721-1733.

Liu P. P., von Dahl C. C., and Klessig D. F. (2011). The extent to which methyl salicylate is required for signaling systemic acquired resistance is dependent on exposure to light after infection. Plant Physiol. 157, 2216-2226.

Lu, H., Rate, D. N., Song, J. T., and Greenberg, J. T. (2003). ACD6, a novel ankyrin protein, is a regulator and an effector of salicylic acid signaling in the *Arabidopsis* defense response. Plant Cell 15, 2408-2420.

Masclaux-Daubresse, C., Clément, G., Anne, P., Routaboul, J. M., Guiboileau, A., Soulay, F., Shirasu, K., and Yoshimoto K. (2014). Stitching together the multiple dimensions of autophagy using metabolomics and transcriptomics reveals impacts on metabolism, development, and plant responses to the environment in *Arabidopsis*. Plant Cell 26: 1857-1877.

Mashiguchi, K., Tanaka, K., Sakai, T., Sugawara, S., Kawaide, H., Natsume, M., Manada, A., Yaeno, T., Shirasu, K., Yao, H., McSteen, P., Zhao, Y., Hayashi, K., Kamiya, Y., and Kasahara, H. (2011). The main auxin biosynthesis pathway in *Arabidopsis*. Proc. Natl. Acad. Sci. USA 108, 18512-18517.

Meneely, K. M., Barr, E. W., Bollinger, J. M. Jr., Lamb, A. L. (2009). Kinetic mechanism of ornithine hydroxylase (PvdA) from *Pseudomonas aeruginosa*: substrate triggering of $O_2$ addition but not flavin reduction. Biochemistry 48, 4371-4376.

Mishina, T. E., and Zeier, J. (2006). The *Arabidopsis* flavin-dependent monooxygenase FMO1 is an essential component of biologically induced systemic acquired resistance. Plant Physiol 141: 1666-1675.

Mishina, T. E., Griebel, T., Geuecke, M., Attaran, E., and Zeier, J. (2008). New insights into the molecular events underlying systemic acquired resistance. Paper 81 in: M Lorito, SL Woo, F Scala, eds, Biology of Plant-Microbe Interactions, Vol 6, International Society for Molecular Plant-Microbe Interactions, St. Paul, MN.

Mölders, W., Buchala, A., and Métraux J.-P. (1996). Transport of salicylic acid in tobacco necrosis virus-infected cucumber plants. Plant Physiol. 112: 787-792.

Moller, B. L. (1976). Lysine Catabolism in Barley (*Hordeum vulgare* L.). Plant Physiol 57, 687-692.

Mou, Z., Fan, W., and Dong, X. (2003). Inducers of plant systemic acquired resistance regulate NPR1 function through redox changes. Cell 113, 935-944.

Moulin, M., Deleu, C., Larher, F., and Bouchereau, A. (2006). The lysine-ketoglutarate reductase-saccharopine dehydrogenase is involved in the osmo-induced synthesis of pipecolic acid in rapeseed leaf tissues. Plant Physiol. Biochem. 44, 474-482.

Murahashi, S.-I., and Shiota, T. (1987). Short-step synthesis of amino acids and N-hydroxyamino acids from amines. Tetrahedron Lett. 28, 6469-6472.

Naumann, C., Hartmann, T., Ober, D. (2002). Evolutionary recruitment of a flavin-dependent monooxygenase for the detoxification of host plant-acquired pyrrolizidine alkaloids in the alkaloid-defended arctiid moth *Tyria jacobaeae*. Proc. Natl. Acad. Sci. USA 99, 6085-6090.

Návarová, H., Bernsdorff, F., Döring, A.-C., and Zeier, J. (2012). Pipecolic acid, an endogenous mediator of defense amplification and priming, is a critical regulator of inducible plant immunity. Plant Cell 24: 5123-5141.

Nawrath, C., and Métraux, J.-P. (1999). Salicylic acid induction-deficient mutants of *Arabidopsis* express PR-2 and PR-5 and accumulate high levels of camalexin after pathogen inoculation. Plant Cell 11: 1393-1404.

Olszak, B., Malinovsky, F. G., Brodersen, P., Grell, M., Giese, H., Petersen, M., and Mundy, J. (2006). A putative flavin-containing mono-oxygenase as a marker for certain defense and cell death pathways. Plant Sci. 170, 614-623.

Olucha, J., and Lamb, A. L. (2011). Mechanistic and structural studies of the N-hydroxylating flavoprotein monooxygenases. Bioorg. Chem. 39, 171-177.

Pálfi, G., and Dézsi, L. (1968). Pipecolic acid as an indicator of abnormal protein metabolism in diseased plants. Plant Soil 29: 285-291.

Park, S.-W., Kaimoyo, E., Kumar, D., Mosher, S., and Klessig, D. F. (2007) Methyl salicylate is a critical mobile signal for plant systemic acquired resistance. Science 318, 113-116.

Riedlmeier, M., Ghirardo, A., Wenig, M., Knappe, C., Koch, K., Georgii, E., Dey, S., Parker, J. E., Schnitzler, J. P., and Vlot, A. C. (2017) Monoterpenes Support Systemic Acquired Resistance within and between Plants. Plant Cell 29, 1440-1459.

Rietz, S., Stamm, A., Malonek, S., Wagner, S., Becker, D., Medina-Escobar, N., Vlot, A. C., Feys, B. J., Niefind, K., and Parker, J. E. (2011). Different roles of Enhanced Disease Susceptibility 1 (EDS1) bound to and dissociated from Phytoalexin Deficient4 (PAD4) in *Arabidopsis* immunity. New Phytol 191: 107-119.

Robinson, M. D., McCarthy, D. J. and Smyth, G. K. (2010). edgeR: a Bioconductor package for differential expression analysis of digital gene expression data. Bioinformatics 26: 139-140.

Rossner, R., Kaeberlein, M., and Leiser, S. F. (2017). Flavin-containing monooxygenases in aging and disease: Emerging roles for ancient enzymes. J. Biol. Chem. 292, 11138-11146.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat. Methods 9, 676-682.

Schlaich, N. L. (2007). Flavin-containing monooxygenases in plants: looking beyond detox. Trends Plant Sci. 12: 412-418.

Schmelz, E. A., Engelberth, J., Tumlinson, J. H., Block, A., and Alborn, H. T. (2004). The use of vapor phase extraction in metabolic profiling of phytohormones and other metabolites. Plant J. 39, 790-808.

Shah, J., and Zeier, J. (2013). Long-distance communication and signal amplification in systemic acquired resistance. Front. Plant Sci. 4, 30.

Sharma, S., Shinde, S., and Verslues, P. E. (2013). Functional characterization of an ornithine cyclodeaminase-like protein of *Arabidopsis thaliana*. BMC Plant Biol. 13, 182.

Sibbesen, O., Koch, B., Halkier, B. A., and Moller, B. L. (1995). Cytochrome P-450TYR is a multi-functional heme-thiolate enzyme catalyzing the conversion of L-tyrosine to p-hydroxyphenylacetaldehyde oxime in the biosynthesis of the cyanogenic glucoside dhurrin in *Sorghum bicolor* (L.) Moench. J. Biol. Chem. 270, 3506-3511.

Slusarenko, A. J., and Schlaich, N. L. (2003). Downy mildew of *Arabidopsis thaliana* caused by *Hyaloperonospora parasitica* (formerly *Peronospora parasitica*). Mol. Plant Pathol. 4, 159-170.

Song, J. T., Lu, H., McDowell, J. M., and Greenberg, J. T. (2004a). A key role for ALD1 in activation of local and systemic defenses in *Arabidopsis*. Plant J. 40, 200-212.

Song, J. T., Lu, H., and Greenberg, J. T. (2004b). Divergent roles in *Arabidopsis thaliana* development and defense of two homologous genes, aberrant growth and death2 and AGD2-LIKE DEFENSE RESPONSE PROTEIN1, encoding novel aminotransferases. Plant Cell 16, 353-366.

Stepanova, A. N., Yun, J., Robles, L. M., Novak, O., He, W., Guo, H., Ljung, K., and Alonso, J. M. (2011). The *Arabidopsis* YUCCA1 flavin monooxygenase functions in the indole-3-pyruvic acid branch of auxin biosynthesis. Plant Cell 23, 3961-3973.

Sticher, L., Mauch-Mani, B., and Métraux, J. P. (1997). Systemic acquired resistance. Annu Rev Phytopathol 35: 235-270.

Sun, T., Zhang, Y., Li, Y., Zhang, Q., Ding, Y., and Zhang, Y. (2015). ChIP-seq reveals broad roles of SARD1 and CBP60g in regulating plant immunity. Nat. Commun. 6, 10159.

Swarbreck, D., et al. (2008). The *Arabidopsis* Information Resource (TAIR): gene structure and function annotation. Nucleic Acids Res 36: D1009-D1014.

Thibaud-Nissen, F., Wu, H., Richmond, T., Redman, J. C., Johnson, C., Green, R., Arias, J., and Town, C. D. (2006). Development of *Arabidopsis* whole-genome microarrays and their application to the discovery of binding sites for the TGA2 transcription factor in salicylic acid-treated plants. Plant J 47: 152-162.

Thimm, O., Blaesing, O., Gibon, Y., Nagel, A., Meyer, S., Krüger, P., Selbig, J., MGller, L. A., Rhee, S. Y., and Stitt, M. (2004). MAPMAN: a user-driven tool to display genomics data sets onto diagrams of metabolic pathways and other biological processes. Plant J 37: 914-939.

Uknes, S., Mauch-Mani, B., Moyer, M., Potter, S., Williams, S., Dincher, S., Chandler, D., Slusarenko, A., Ward, E., and Ryals J. (1992). Acquired resistance in *Arabidopsis*. Plant Cell 4, 645-656.

Vernooij, B., Friedrich, L., Morse, A., Reist, R., Kolditzjawhar, R., Ward, E., Uknes, S., Kessmann, H., and Ryals, J. (1994). Salicylic acid is not the translocated signal responsible for inducing systemic acquired resistance but is required in signal transduction. Plant Cell 6, 959-965.

Vogel-Adghough, D., Stahl, E., Návarová, H., and Zeier, J. (2013). Pipecolic acid enhances resistance to bacterial infection and primes salicylic acid and nicotine accumulation in tobacco. Plant Sig Behav 8: e26366.

Wang, L., Tsuda, K., Truman, W., Sato, M., Nguyen, L. V., Katagiri, F., and Glazebrook J. (2011). CBP60g and SARD1 play partially redundant critical roles in salicylic acid signaling. Plant J. 67, 1029-1041.

Wang, C., El-Shetehy, M., Shine, M. B., Yu, K., Navarre, D., Wendehenne, D., Kachroo, A., and Kachroo P. (2014). Free radicals mediate systemic acquired resistance. Cell Rep. 7, 348-355.

Wildermuth, M. C., Dewdney, J., Wu, G., and Ausubel, F. M. (2001). Isochorismate synthase is required to synthesize salicylic acid for plant defence. Nature 414: 562-565.

Wittstock, U., and Halkier, B. A. (2000) Cytochrome P450 CYP79A2 from *Arabidopsis thaliana* L. catalyzes the conversion of L-phenylalanine to phenylacetaldoxime in the biosynthesis of benzylglucosinolate. J. Biol. Chem. 275, 14659-14666.

Wu, Y., Zhang, D., Chu, J. Y., Boyle, P., Wang, Y., Brindle, I. D., De Luca, V., and Després, C. (2012). The *Arabidopsis* NPR1 protein is a receptor for the plant defense hormone salicylic acid. Cell Reports 1: 639-647.

Yoshimoto, N., Onuma, M., Mizuno, S., Sugino, Y., Nakabayashi, R., Imai, S., Tsuneyoshi, T., Sumi, S., and Saito, K. (2015). Identification of a flavin-containing S-oxygenating monooxygenase involved in alliin biosynthesis in garlic. Plant J. 83, 941-951.

Zacharius, R. M., Thompson, J. F., and Steward, F. C. (1954). The Detection, Isolation and Identification of L(−)Pipecolic Acid in the Non-protein Fraction of Beans (*Phascolus vulgaris*) 1, 2. J. Am. Chem. Soc. 76, 2908-2912.

Zeier, J. (2013). New insights into the regulation of plant immunity by amino acid metabolic pathways. Plant Cell Environ 36: 2085-2103.

Zeng, G. (1998). Sticky-end PCR: new method for subcloning. BioTechniques 25, 206-208.

Ziegler, D. M. (2002). An overview of the mechanism, substrate specificities, and structure of FMOs. Drug. Metab. Rev. 34, 503-511.

Zhang, Z., Lenk, A., Andersson, M. X., Gjetting, T., Pedersen, C., Nielsen, M. E., Newman, M. A., Hou, B. H., Somerville, S. C., and Thordal-Christensen, H. (2008). A lesion-mimic syntaxin double mutant in *Arabidopsis* reveals novel complexity of pathogen defense signaling. Mol. Plant 1, 510-527.

Zhao, Y., Christensen, S. K., Fankhauser, C., Cashman, J. R., Cohen, J. D., Weigel, D., and Chory, J. (2001). A role for flavin monooxygenase-like enzymes in auxin biosynthesis. Science 291, 306-309.

Zhou N., Tootle T. L., Tsui F., Klessig D. F., and Glazebrook J. (1998). PAD4 functions upstream from salicylic acid to control defence responses in *Arabidopsis*. Plant Cell 10: 1021-1030.

The invention claimed is:

1. A method for inducing acquired resistance in a plant to a plant pathogen, comprising
    a) obtaining or providing a composition comprising 1-hydroxypiperidine-2-carboxylic acid or a methyl ester thereof, and
    b) contacting a plant with said composition, thereby inducing acquired resistance in the plant.

2. The method of claim 1, wherein said acquired resistance is induced by priming said plant to induce a resistance response to a plant pathogen.

3. The method of claim 1, wherein the plant is a monocot or dicot.

4. The method of claim 1, wherein said plant pathogen is a bacterium, fungus, oomycete, or virus.

5. The method of claim 1, wherein said plant pathogen is a biotrophic or hemibiotrophic plant pathogen.

6. The method of claim 1, wherein said plant is contacted with said composition by contacting the roots, shoots or leaves of the plants with said composition.

7. The method of claim 1, wherein said plant is contacted with said composition at least once per month.

8. The method of claim 1, wherein said composition comprises 1-hydroxypiperidine-2-carboxylic acid or a methyl ester thereof,
    wherein the concentration of the 1-hydroxypiperidine-2-carboxylic acid or methyl ester thereof in the composition is from 0.1 mM to 10 mM.

9. The method of claim 1, wherein said composition further comprises at least one plant nutrient and/or at least one further plant protection product or salt or derivative thereof.

10. A plant seed coated with a composition comprising 1-hydroxypiperidine-2-carboxylic acid or a methyl ester thereof.

11. An irrigation system filled with irrigation water comprising 1-hydroxypiperidine-2-carboxylic acid or a methyl ester thereof,
    wherein the concentration of the 1-hydroxypiperidine-2-carboxylic acid or methyl ester thereof in the irrigation water is from 0.1 mM to 10 mM.

12. A fertilizer composition comprising 1-hydroxypiperidine-2-carboxylic acid or a methyl ester thereof,
    wherein the concentration of the 1-hydroxypiperidine-2-carboxylic acid or methyl ester thereof in the fertilizer composition is from 0.1 mM to 10 mM.

13. The fertilizer composition of claim 12, wherein said fertilizer composition is a nitrogen fertilizer, a phosphate fertilizer, or a potassium fertilizer, or wherein said fertilizer is a NPK fertilizer.

14. The method of claim 1, wherein said composition is contacted with the plant prior to the plant pathogen attack.

* * * * *